United States Patent
Komiya et al.

(10) Patent No.: US 7,582,055 B2
(45) Date of Patent: *Sep. 1, 2009

(54) ENDOSCOPE SYSTEM

(75) Inventors: Takaaki Komiya, Akiruno (JP);
Kazushi Murakami, Hino (JP); Hiroaki Ichikawa, Hachioji (JP); Yoshio Onuki, Hachioji (JP); Yasuhito Kura, Hachioji (JP); Takehiro Nishiie, Akishima (JP)

(73) Assignee: Olympus Medical Systems Corp., Tokyo (JP)

( * ) Notice: Subject to any disclaimer, the term of this patent is extended or adjusted under 35 U.S.C. 154(b) by 440 days.

This patent is subject to a terminal disclaimer.

(21) Appl. No.: 11/501,356

(22) Filed: Aug. 9, 2006

(65) Prior Publication Data

US 2008/0039685 A1   Feb. 14, 2008

(51) Int. Cl.
*A61B 1/00* (2006.01)
(52) U.S. Cl. .......................... 600/106; 600/104; 606/46
(58) Field of Classification Search ......... 600/104–106, 600/114; 606/1, 46
See application file for complete search history.

(56) References Cited

U.S. PATENT DOCUMENTS

| | | | | |
|---|---|---|---|---|
| 5,431,645 | A * | 7/1995 | Smith et al. | 606/1 |
| 5,971,929 | A * | 10/1999 | Sakamoto et al. | 600/462 |
| 6,231,565 | B1 | 5/2001 | Tovey et al. | |
| 6,321,106 | B1 | 11/2001 | Lemelson | |
| 6,764,439 | B2 * | 7/2004 | Schaaf et al. | 600/106 |
| 6,793,652 | B1 | 9/2004 | Whitman et al. | |
| 7,048,684 | B2 * | 5/2006 | Parasher et al. | 600/104 |
| 2002/0087048 | A1 * | 7/2002 | Brock et al. | 600/114 |
| 2002/0107538 | A1 * | 8/2002 | Shibata et al. | 606/169 |
| 2005/0192475 | A1 * | 9/2005 | Okada | 600/106 |
| 2006/0106281 | A1 * | 5/2006 | Boulais et al. | 600/104 |

FOREIGN PATENT DOCUMENTS

| | | |
|---|---|---|
| EP | 1 543 765 A1 | 6/2005 |
| EP | 1 568 306 A1 | 8/2005 |
| EP | 1 815 810 A1 | 8/2007 |
| JP | 57-190541 | 11/1982 |
| JP | 05-337121 | 12/1993 |
| JP | 06-055473 | 3/1994 |
| JP | 2000-000207 | 1/2000 |

* cited by examiner

Primary Examiner—John P Leubecker
(74) Attorney, Agent, or Firm—Scully, Scott, Murphy & Presser, P.C.

(57) ABSTRACT

An endoscope system comprises multiple types of treatment tools including a treatment-tool insertion unit, and a function unit having a function for performing treatment; an electrically-driven operation device which electrically drives the function unit; an electrically-driven advance/retreat device which electrically drives the treatment-tool insertion unit; a control device including at least one of a control unit for outputting a control signal to the electrically-driven advance/retreat device and the electrically-driven operation device, and an operating program corresponding to a treatment tool; and an operation instructing device including a first operating instruction unit for outputting an instruction signal for placing the electrically-driven operation device and the electrically-driven advance/retreat device into a manually-driven operating state, and a second operating instruction unit for outputting an instruction signal for placing the electrically-driven operation device and the electrically-driven advance/retreat device into a programmed-control state by the operating program. When receiving either of the signal from the first operating instruction unit or the signal from the second operating instruction unit, the control unit performs control for outputting the control signal corresponding to the received signal to at least one of the electrically-driven advance/retreat device and the electrically-driven operation device.

20 Claims, 28 Drawing Sheets

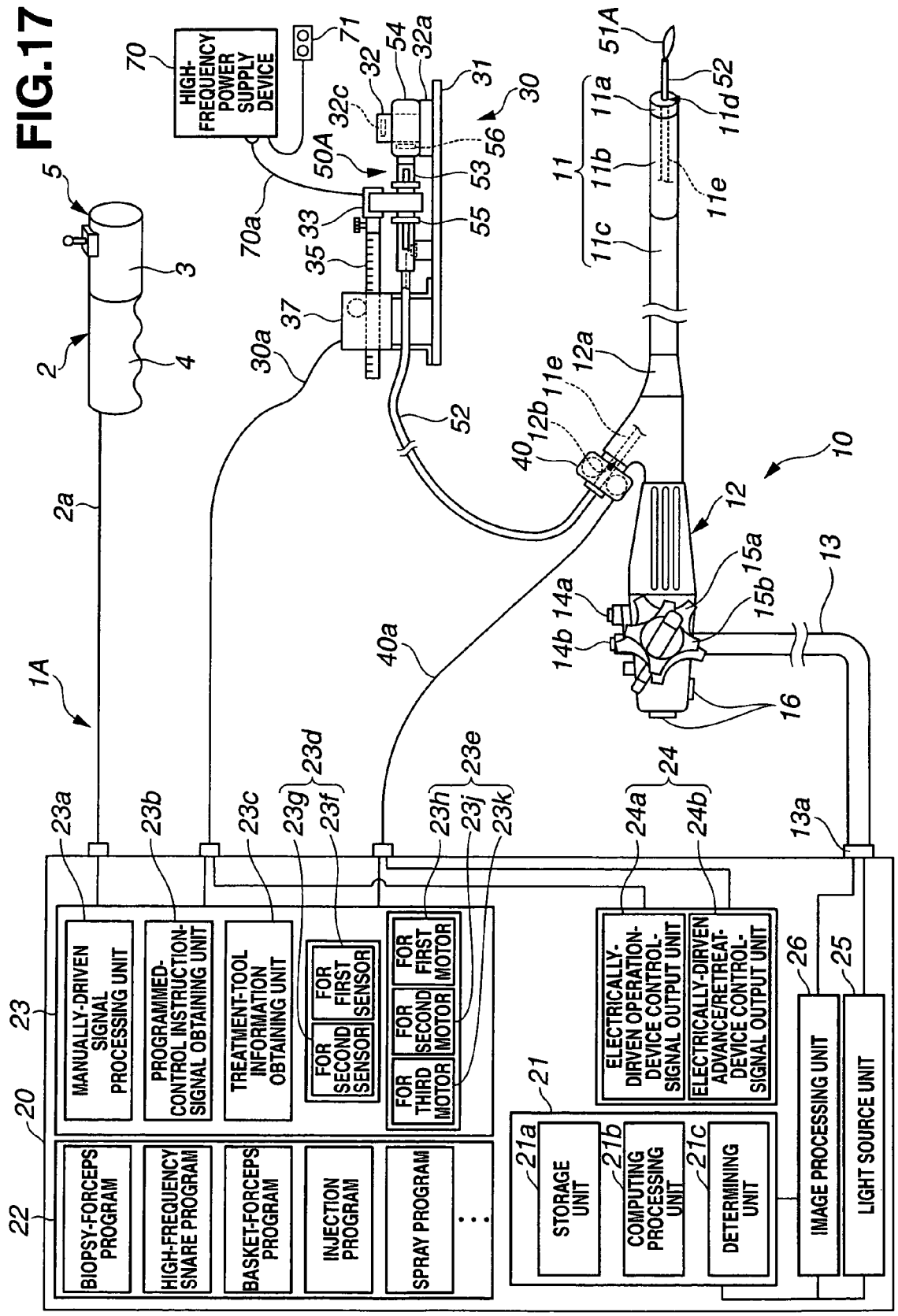

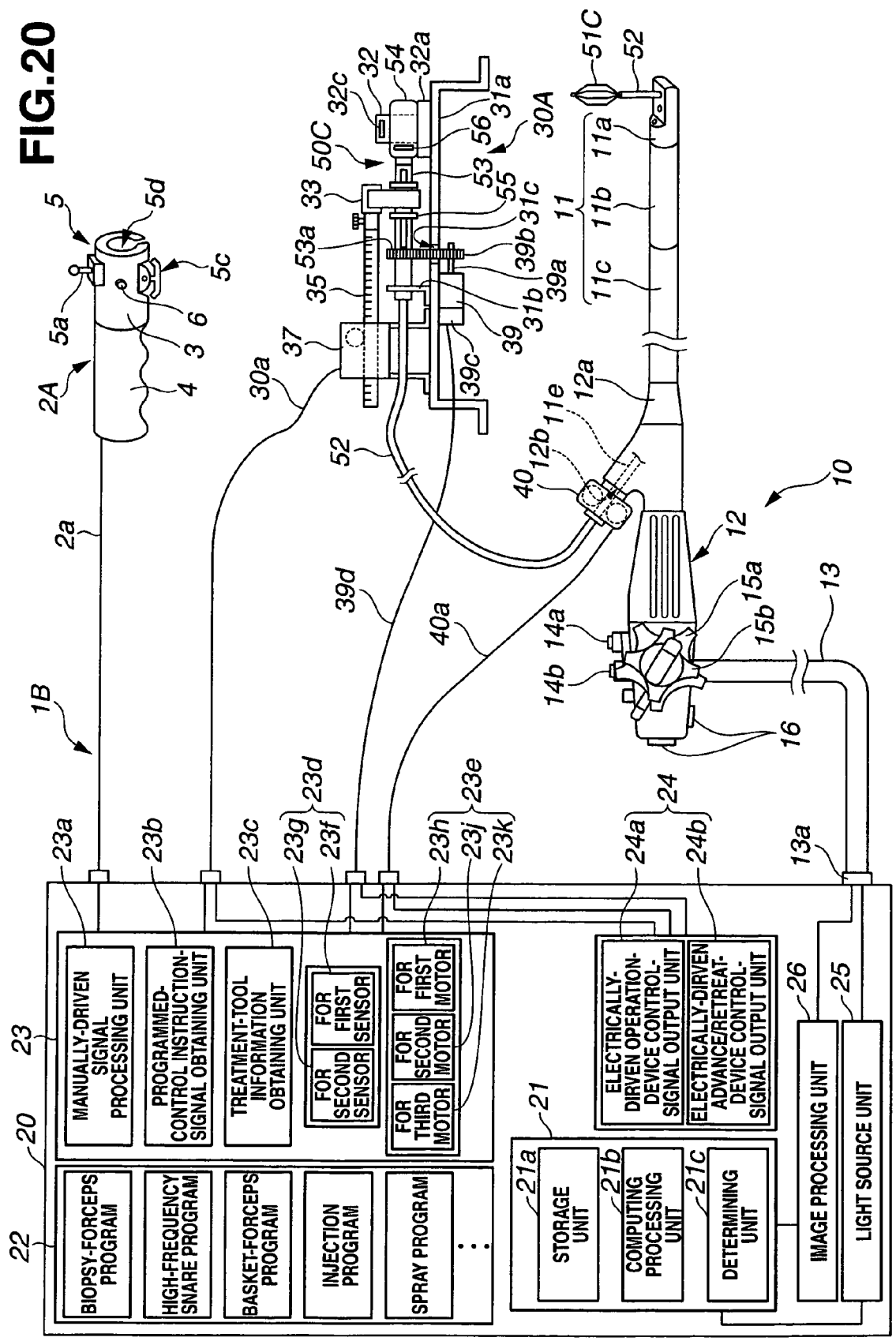

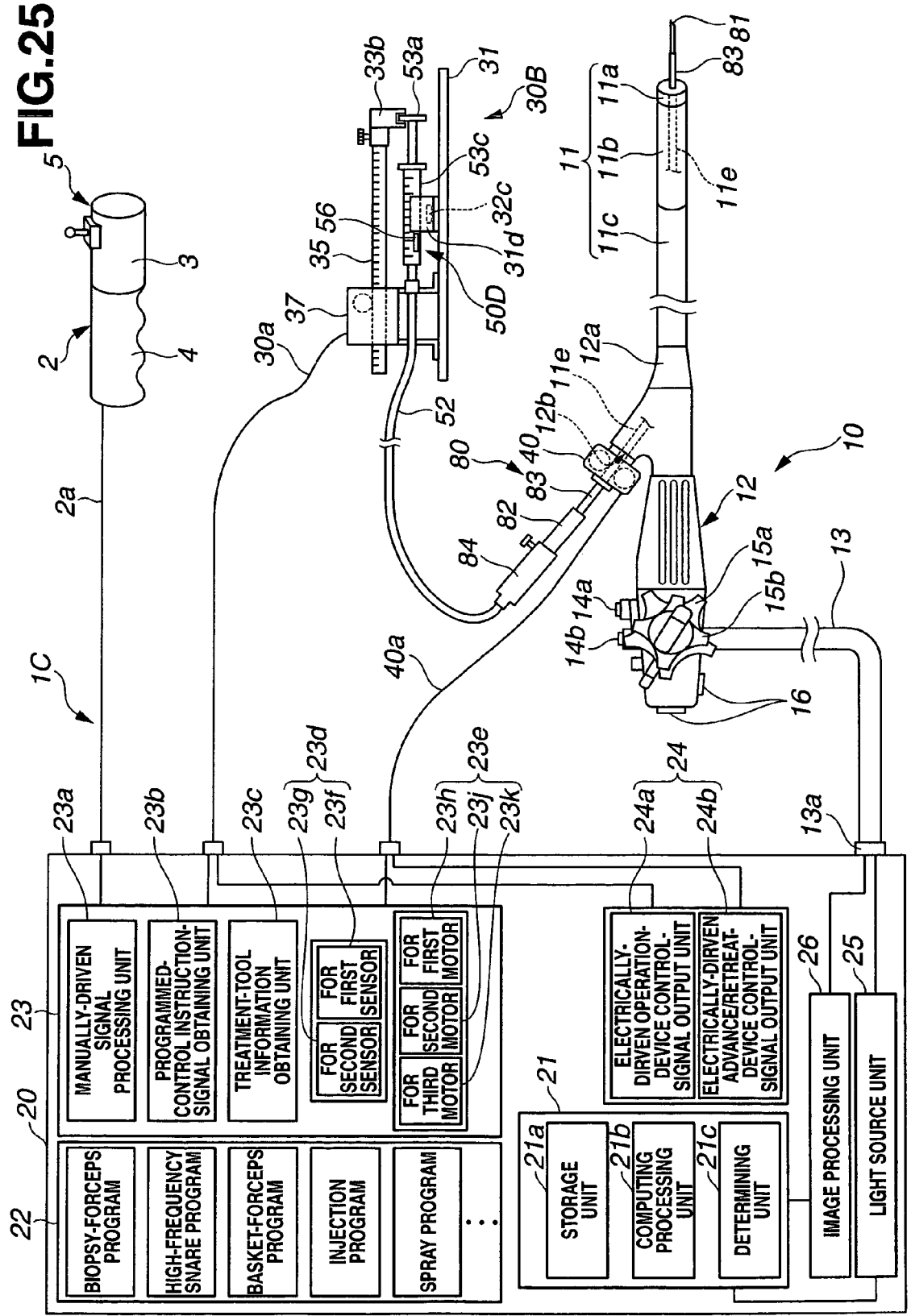

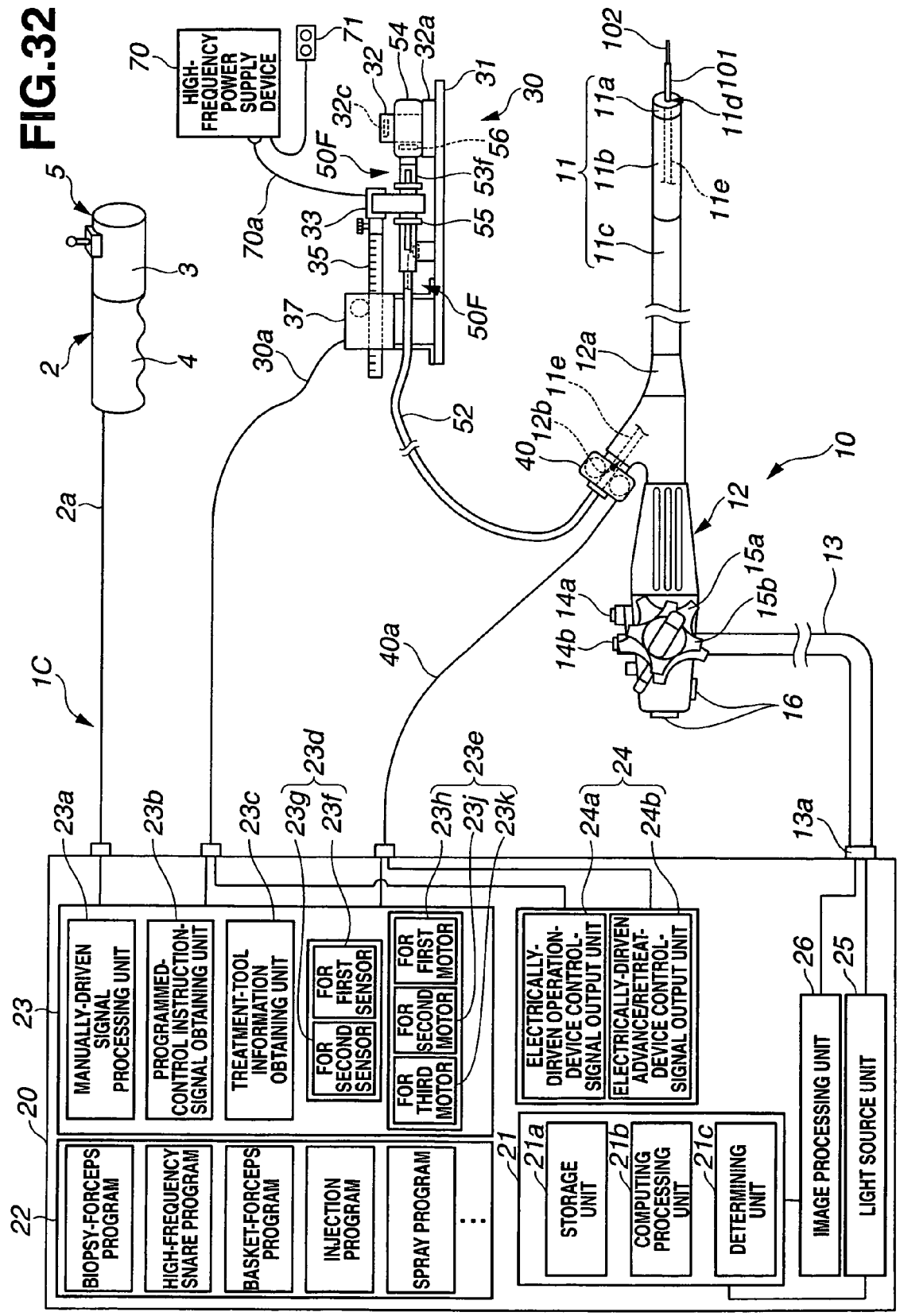

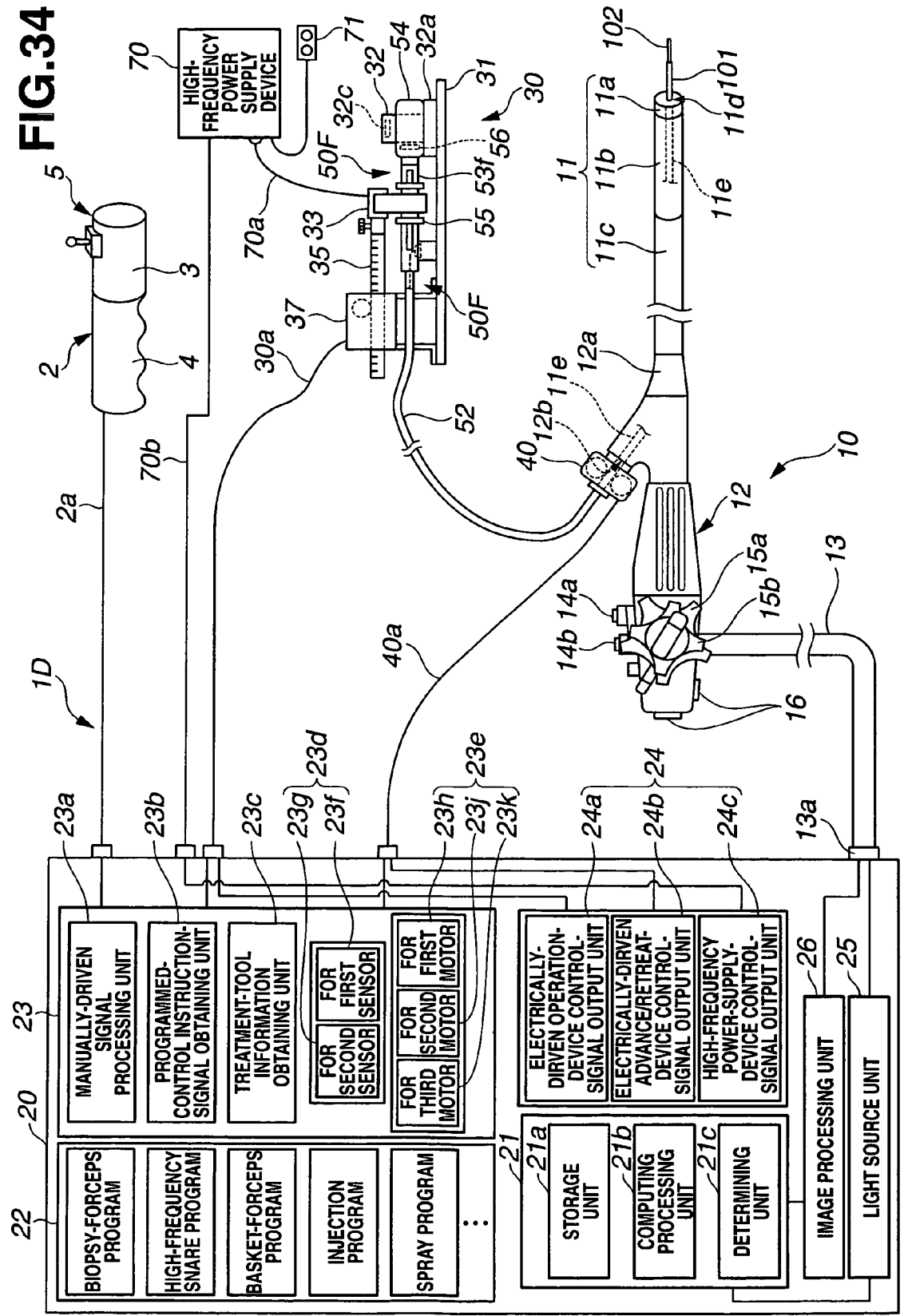

ENDOSCOPE SYSTEM

BACKGROUND OF THE INVENTION

1. Field of the Invention

The present invention relates to an endoscope system including an endoscope operation assisting device for facilitating operation of various types of treatment tools to be used together with an endoscope.

2. Description of the Related Art

In recent years, endoscopes have been widely used in the medical-application field. An endoscope comprises a slender insertion unit, and an operation unit provided at the base of this insertion unit. Generally, a bending portion which is bendable is provided at the tip side of the slender insertion unit. A knob for bending and operating the bending portion, and various types of switches and so forth for performing various types of operations of endoscope functions are provided in the operation unit.

With an endoscope to be employed for the medical-application field, when performing observation of a body cavity organ, an insertion unit is inserted into the body cavity of a subject. Also, with the endoscope, various types of treatment can be performed by introducing a treatment tool into the body cavity via a treatment-tool channel provided in the insertion unit.

In the event of inserting a treatment tool into the treatment-tool channel of the endoscope, a surgeon holds a sheath serving as the insertion unit of the treatment tool, and inserts the sheath into the treatment-tool channel manually. However, insertion work by hand feeding takes a lot of efforts. Also, it takes considerable attention to insert, for example, a sheath portion reaching 2 m without buckling, and preventing the sheath portion from coming into contact with an unclean area, which has been troublesome and intricate work for a worker.

In order to solve such a problem, for example, Japanese Unexamined Patent Application Publication No. 57-190541 has disclosed an endoscope which enables the sheath of a treatment tool to be inserted into a treatment-tool channel mechanically.

Also, Japanese Unexamined Patent Application Publication No. 2000-207 has disclosed an endoscope treatment-tool insertion/removal device which enables insertion operation of a treatment tool, and operation of a treatment portion to be performed mechanically based on operations of a foot switch.

Even in the event of using the above endoscope, and the above endoscope treatment-tool insertion/removal device, when performing treatment maneuvers by actually operating a treatment tool, the treatment portion is operated by a surgeon's operation at the side toward the surgeon. Accordingly, the results of treatment depend on a surgeon's maneuver skill. In other words, a huge gap is caused in maneuver skill between an inexperienced physician and an experienced physician.

SUMMARY OF THE INVENTION

An endoscope system comprises: multiple types of treatment tools including a treatment-tool insertion unit to be inserted in a treatment-tool channel provided in the insertion unit of an endoscope, and a function unit having a function for performing a certain treatment, which is introduced within a body cavity, provided at the tip side of the treatment-tool insertion unit; an electrically-driven operation device which electrically drives the function unit; an electrically-driven advance/retreat device which electrically drives the treatment-tool insertion unit; a control device, which is electrically connected to the electrically-driven advance/retreat device and the electrically-driven operation device, including at least one of a control unit for outputting a control signal to the electrically-driven advance/retreat device and the electrically-driven operation device, and an operating program corresponding to a treatment tool; an operation instructing device, which is electrically connected to the control device, including a first operating instruction unit for outputting a first instruction signal for placing the electrically-driven operation device and the electrically-driven advance/retreat device into a manually-driven operating state, and a second operating instruction unit for outputting a second instruction signal for placing the electrically-driven operation device and the electrically-driven advance/retreat device into a programmed-control state by the operating program.

When receiving a first instruction signal output from the operation instructing device, the control unit of the control device outputs the control signal corresponding to the first instruction signal to at least one of the electrically-driven advance/retreat device and the electrically-driven operation device, and when receiving a second instruction signal output from the operation instructing device, the control unit of the control device executes the operating program, and outputs the control signal in accordance with an instruction of the operating program to at least one of the electrically-driven advance/retreat device and the electrically-driven operation device.

The above and other objects, features and advantages of the invention will become more clearly understood from the following description referring to the accompanying drawings.

BRIEF DESCRIPTION OF THE DRAWINGS

FIG. 2 is a diagram illustrating an operation instructing device in a state of being gripped by the hand of a surgeon or the like;

FIG. 17 is a diagram describing the overall configuration of an endoscope system in which a treatment tool is a high-frequency snare;

FIG. 20 is a diagram describing the overall configuration of an endoscope system wherein a treatment tool is a basket forceps;

FIG. 25 is a diagram describing the overall configuration of an endoscope treatment system including a puncture needle and an injector as treatment tools for injecting the liquid of the injector into tissue;

FIG. 32 is a diagram describing the overall configuration of an endoscope system wherein a treatment tool is a marking device;

FIG. 34 is an overall diagram describing another configuration of an endoscope system wherein a treatment tool is a marking device.

DETAILED DESCRIPTION OF THE PREFERRED EMBODIMENTS

Hereinafter, embodiments of the present invention will be described with reference to the drawings.

One embodiment of the present invention will be described with reference to FIG. 1 through FIG. 16.

Figure 1:
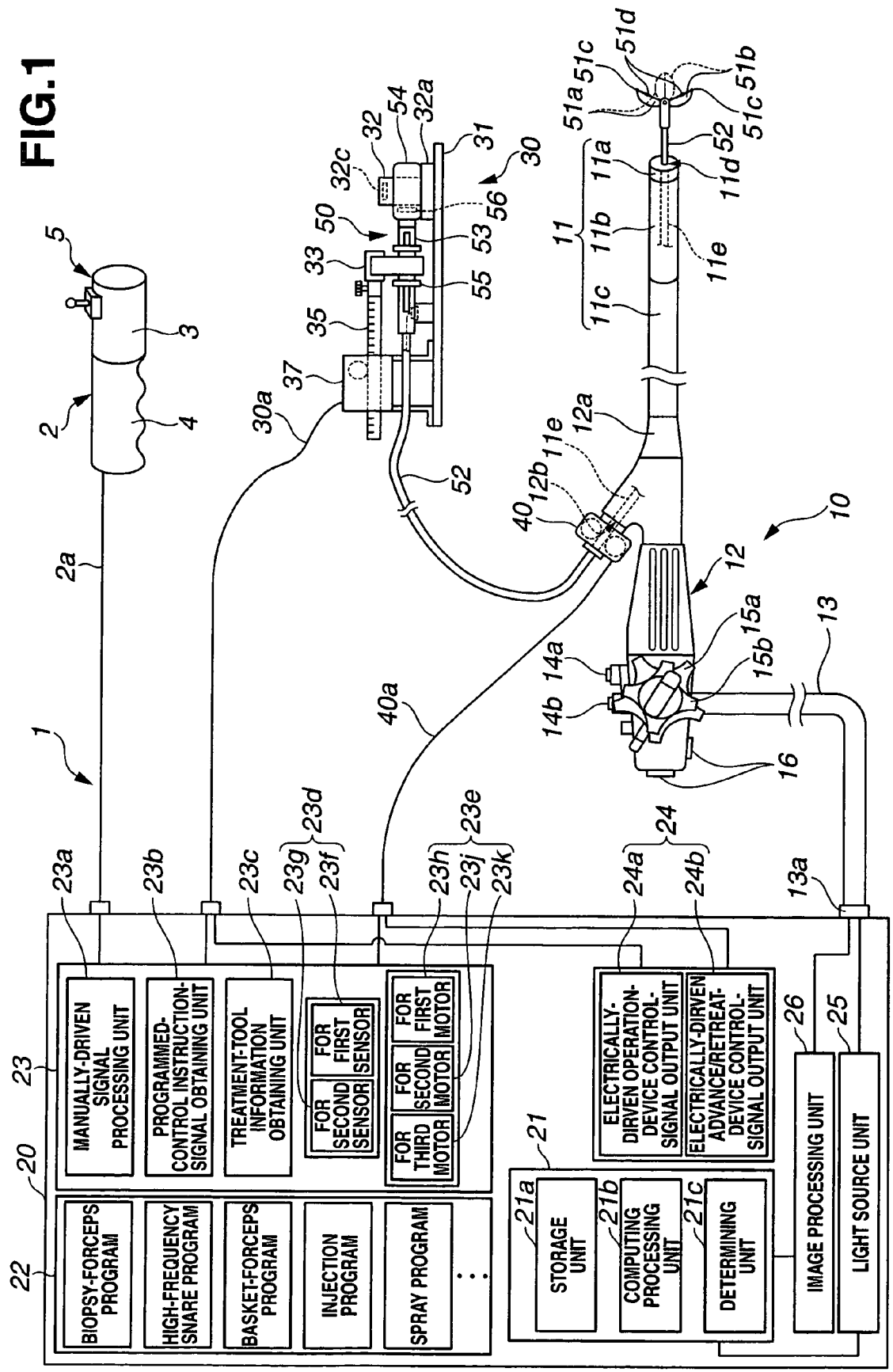
FIG. 1 is a diagram describing an overall configuration of an endoscope system wherein a treatment tool is a biopsy forceps.

As illustrated in FIG. 1, an endoscope system 1 principally comprises an operation instructing device 2, an endoscope 10, a control device 20, a treatment-tool operation-unit electrically-driven operation device (hereinafter, referred to as electrically-driven operation device) 30, and a treatment-tool insertion-unit electrically-driven advance/retreat device (hereinafter, referred to as electrically-driven advance/retreat device) 40. With the present embodiment, the operation instructing device 2, control device 20, electrically-driven operation device 30, and electrically-driven advance/retreat device 40 make up an endoscope operation assisting device.

The endoscope 10 comprises an insertion unit 11, an operation unit 12, and a universal cord 13. The operation unit 12 also serves as a gripper, and is disposed at the base side of the insertion unit 11. The universal cord 13 is extended to the side portion of the operation unit 12, and a connector 13a at base thereof is connected to the control device 20.

The insertion unit 11 is configured by a hard tip portion 11a, a bendable bending portion 11b, and a flexible tube portion 11 having flexibility being serially provided in order from the tip side. The operation unit 12 is provided with a folding-prevention portion 12a connected to the base of the flexible tube portion 11c. The operation unit 12 is provided with an air feed/water feed button 14a for feeding air and water, a suction button 14b for performing suction, bending knobs 15a and 15b for bending and operating the bending portion 11b, and various types of switch 16 for performing control as to an endoscope image displayed on the screen of a display device, which is captured by image capturing means such as a CCD or the like provided at the tip portion 11a, and so forth.

The endoscope 10 includes a treatment-tool channel 11e communicating between a treatment-tool opening 12b and the tip opening 11d of the tip portion 11a. The treatment-tool channel 11e is an introducing path for introducing a treatment tool into a body cavity. Various types of treatment tool such as a later-described biopsy forceps, high-frequency snare, basket forceps, and so forth are introduced into a body cavity via this treatment-tool channel 11e.

With the control device 20, inside thereof principally comprises a CPU 21 serving as a control unit, a storage device 22 such as a hard disk or the like serving as a storage unit, a signal input unit 23, a control-signal output unit 24, and so forth.

An operating program for operating a treatment tool is registered on the storage device 22 for each treatment tool. The operating programs for operating a treatment tool are programs for operating a treatment tool introduced into a body cavity via the treatment-tool channel 11e of the endoscope 10 as with an experienced surgeon operating that. With the present embodiment, the storage device 22 is registered with, for example, a biopsy-forceps program, high-frequency snare program, basket-forceps program, injector program, spray program, marking program, and so on as operating programs.

The CPU 21 comprises, for example, a storage unit 21a, a computing processing unit 21b, a determining unit 21c, and so forth. The signal input unit 23 principally comprises a manually-driven signal determining processing unit (hereinafter, referred to as manually-driven signal processing unit) 23a, a programmed-control instruction-signal obtaining unit (hereinafter, abbreviated as instruction-signal obtaining unit) 23b, a treatment-tool information obtaining unit 23c, a sensor obtaining unit 23d, and a motor rotating-speed obtaining unit 23e.

The sensor obtaining unit 23d comprises multiple sensor obtaining units, for example, a first sensor obtaining unit 23f, and a second sensor obtaining unit 23g. The motor rotating-speed obtaining unit 23e comprises multiple motor obtaining units, for example, a first motor obtaining unit 23h, a second motor obtaining unit 23j, and a third motor obtaining unit 23k.

The control-signal output unit 24 comprises, for example, an electrically-driven operation device control-signal output unit (hereinafter, referred to as first output unit) 24a for outputting a control signal to the electrically-driven operation device 30, and an electrically-driven advance/retreat-device control-signal output unit (hereinafter, referred to as second output unit) 24b for outputting a control signal to the electrically-driven advance/retreat device 40.

Note that reference numeral 25 denotes a light source unit, which controls an illumination state of illumination light which illuminates the inside of a body cavity. Reference numeral 26 denotes an image processing unit, which performs control of an image capturing device included in the endoscope 10, processing for generating a video signal from an electric signal to be transmitted from the image capturing device, and so forth. Accordingly, the control device 20 is electrically connected with a display device, or the control device 20 includes a display device such as liquid-crystal monitor (not shown) for displaying an endoscope image in response to receiving a video signal processed at the image processing unit 26.

The control device 20 is electrically connected with the operation instructing device 2, electrically-driven operation device 30, and electrically-driven advance/retreat device 40 via signal cables 2a, 30a, and 40a. Note that in FIG. 1, the electrically-driven operation device 30 is installed with a handle portion 53 serving as a treatment tool, for example, serving as the operation unit of a biopsy forceps 50. The electrically-driven operation device 30 performs an opening/closing operation of a tissue sampling unit 51 serving as the function unit of the biopsy forceps 50 by moving the handle portion 53. Also, the electrically-driven advance/retreat device 40 is installed in a treatment-tool attachment 12c including the treatment-tool opening 12b of the endoscope 10. The electrically-driven advance/retreat device 40 performs advance/retreat movement of a sheath 52 serving as the treatment-tool insertion unit of the biopsy forceps 50.

The handle operation of the electrically-driven operation device 30, and the advance/retreat movement of the electrically-driven advance/retreat device 40 are performed in either of a manually-operated state by the operation instructing device 2, or a programmed-control state based on the biopsy-forceps program registered on the storage device 22.

Now, the configuration of the biopsy forceps 50 will be described.

The biopsy forceps 50 comprises a tissue sampling unit 51, a slender sheath 52, and a handle portion 53 in order from the tip side. The tissue sampling unit 51 is provided at the tip of the sheath 52. The tissue sampling unit 51 includes a pair of biopsy cups 51a and 51b, and the biopsy cups 51a and 51b are configured so as to be openable and closable. The biopsy cups 51a and 51b are each provided with a first sensor 51c which is a tissue contact pressure detection sensor serving as first detection means, and a second sensor 51d which is a closed-state detection sensor serving as second detection means. The first sensor 51c is provided at the tip side of at least one of the cups 51a and 51b. The one second sensor 51d or a pair of the second sensors 51d are provided so as to detect being in contact in the position facing the cups 51a and 51b, i.e., so as to detect a closed state. Note that the maximum outer shape of the tissue sampling unit 51 is configured so as to be a size which can be inserted into the treatment-tool channel 11e, or so as to be smaller than the outside diameter dimension of the insertion unit 11 in a closed state of the cups 51a and 51b.

The tissue contact pressure detection sensor detects, by the tip side faces of the biopsy cups 51a and 51b coming into contact with a body tissue, contact pressure thereof, and outputs a pressure detection signal (hereinafter, referred to as pressure signal) serving as the electric signal corresponding change in pressure thereof. The closed-state detection sensor outputs a closed-state detection signal (hereinafter, referred to as closed signal) to the control device 20 at the time of a closed state in which the biopsy cups 51a and 51b are in contact with each other.

Signal lines which are not shown are extended from the respective sensors 51c and 51d. The other end portions of the signal lines are connected to the electric contact point (see reference numeral 57 in FIG. 9) provided at a slider 55 passing through the sheath 52.

An operating wire (not shown) other than the above signal lines is inserted into the sheath 52 of the biopsy forceps 50. The operating wire advances or retreats depending on operation of the handle portion 53. That is to say, the tissue sampling unit 51 changes from an open state to a closed state, or to a reversed state thereof, by operating the handle portion 53 to advance or retreat the operating wire.

The handle portion 53 comprises a finger-hooking ring 54 and a slider 55. The finger-hooking ring 54 includes a hole portion where the thumb of a user is disposed for example. The slider 55 includes a pair of flanges where the second finger and third finger of the user are disposed on the way thereof. The finger-hooking ring 54 has built in, for example, a non-contact IC chip (hereinafter, referred to as IC chip) 56 making up the treatment-tool information unit side of the RFID serving as treatment-tool identifying means. Treatment-tool information indicating the type of treatment tool thereof is registered on the IC chip 56.

Description will be made regarding the operation instructing device 2 with reference to FIG. 1 through FIG. 4.

Figure 2:
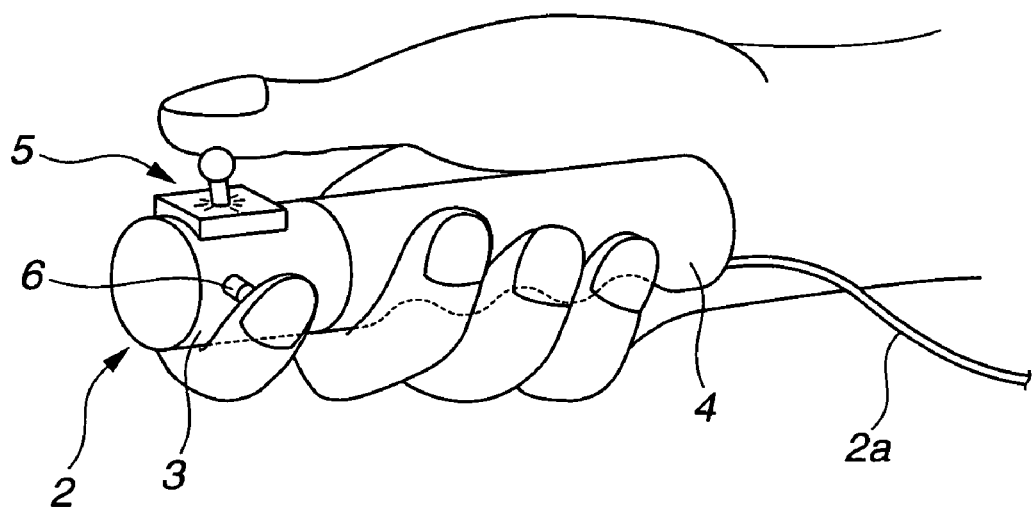

As illustrated in FIG. 1 and FIG. 2, the operation instructing device 2 comprises, for example, a general cylindrical hard main body portion 3, and a grip body 4 to be serially connected to the main body portion 3. The grip body 4 is made up of, for example, an elastic member, and the above signal cable 2a is extended from the base of the grip body 4. A fitting protruding portion 3a is protruded from the center of the base face of the main body portion 3. The main body portion 3 and the grip body 4 are formed in an integrated manner by the fitting protruding portion 3a being fitted into a fitting hole opened in the tip face of the grip body 4. A grip portion 4a configured in an uneven shape is provided on the grip body 4. The grip portion 4a is provided on the side face which assumes the positional relation of the opposite side of the manually-driven operation unit 5 of the main body portion 3. A surgeon grips the grip portion 4a, whereby slippage is prevented, and the surgeon can grip the operation instructing device 2 in a sure manner.

The side circumferential face of the main body portion 3 is provided with a manually-driven operation instructing unit (hereinafter, referred to as manually-driven operation unit) 5 serving as a first operation instructing unit, and a programmed-control instructing unit (hereinafter, referred to as programmed instruction unit) 6 serving as a second operation instructing unit.

Note that with the operation instructing device 2 thus configured, hereinafter in the following description, the tip face side of the main body portion 3 is referred to as the tip side, the base face side of the grip body 4 as the base side, the manually-driven operation unit 5 side provided in the main body portion 3 as the upper portion, and the grip portion 4a side provided on the grip body 4 as the lower portion. Also, multiple signal lines are inserted into the signal cable 2a.

Figure 3:
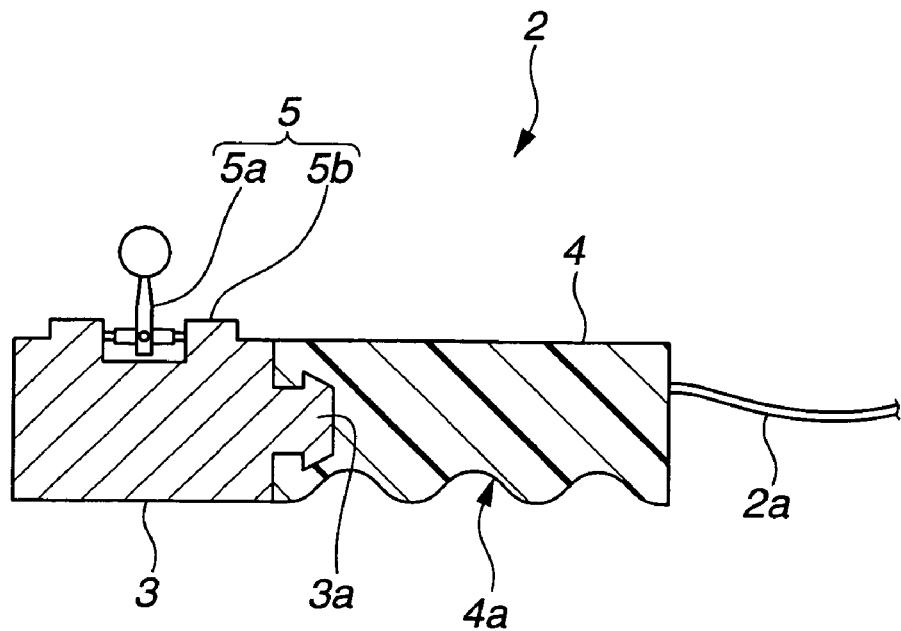
FIG. 3 is a cross-sectional view of the operation instructing device.

As illustrated in FIG. 3, the manually-driven operation unit 5 is a so-called joystick-type operating lever 5a which is leaned and operated, which is a return-to-origin-type switch which can be operated with two axes. The operating lever 5a is configured so as to be supported by an operating lever supporting portion 5b. The manually-driven operation unit 5 outputs an operation instructing signal serving as a first instruction signal to the manually-driven signal processing unit 23a of the signal input unit 23.

In the event that a treatment tool is the biopsy forceps 50 including the tissue sampling unit 51 which can be opened and closed at the tip side of the slender sheath 52, upon the user leaning and operating the operating lever 5a of the manually-driven operation unit 5, the operation instructing signal corresponding to lever operation thereof is output to the control device 20 from the manually-driven operation unit 5.

Specific description will be made as follows.

In the event of the operating lever 5a being leaned and operated toward the tip side, an advance signal serving as a signal for instructing operation for advancing the sheath 52 is output. In the event of the operating lever 5a being leaned and operated toward the base side, a retreat signal serving as a signal for instructing operation for retreating the sheath 52 is output. In the event of the operating lever 5a being leaned and operated to the left side as viewed from the upper direction toward the tip, an opening signal for instructing operation of opening the tissue sampling unit 51 is output. In the event of the operating lever 5a being leaned and operated to the right side as viewed from the upper direction toward the tip, a closing signal for instructing operation for closing the tissue sampling unit 51 is output.

Figure 4:
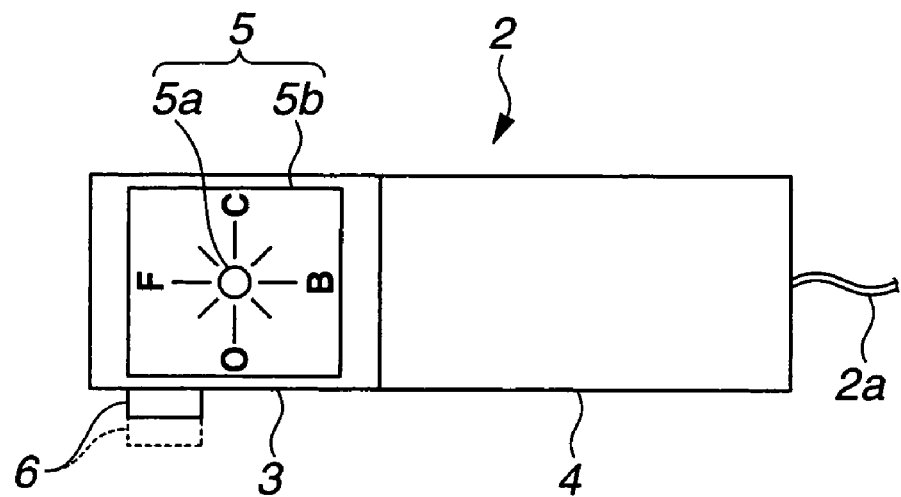
FIG. 4 is a plan view of the operation instructing device as viewed from above.
Figure 5:
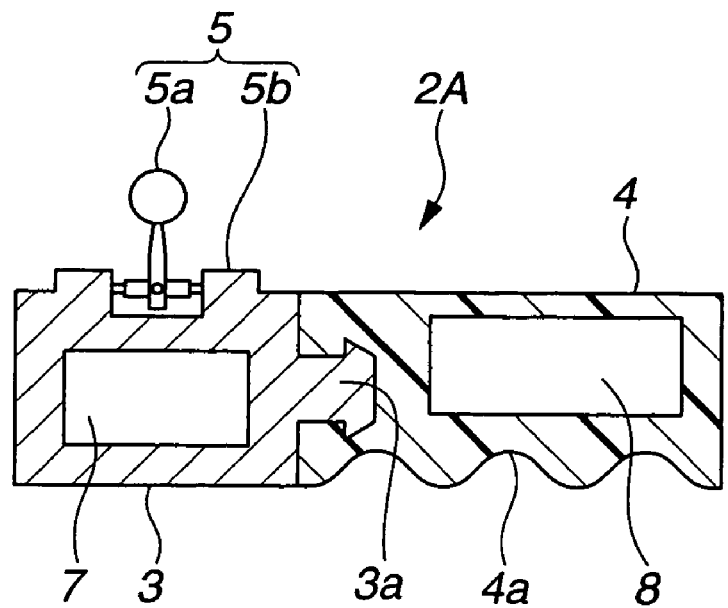
FIG. 5 is a cross-sectional view for describing a modification of the operation instructing device.

An arrangement may be made wherein the top face of the operating lever supporting portion 5b of the manually-driven operation unit 5 is provided with a reference mark indicating the operating instruction of the biopsy forceps 50 corresponding to the leaned direction of the operating lever 5a. Examples of the reference mark include letters such as illustrated in FIG. 4. Reference mark "F" indicating advancement toward the tip side of the operating lever supporting portion 5b, reference mark "B" indicating retreat toward the base side, reference mark "O" indicating opening operation to the left side as viewed from the upper direction toward the tip, and reference mark "C" indicating closing operation to the right side as viewed from the upper direction toward the tip are printed. Thus, the user can readily understand the relation between the leaned direction of the lever and operation of a treatment tool.

Note that in the event of the operating lever 5a being leaned and operated to an intermediate area of the reference marks indicating the tip direction, base direction, left direction, and right direction, an advance signal or retreat signal, and an opening signal or closing signal are configured so as to be output simultaneously. Also, advance/retreat speed and opening/closing speed are arranged so as to be changed depending on difference of a leaning angle when leaning and operating the operating lever 5a. For example, as the leaning angle of the operating lever 5a is greatly leaned as to the initial position, advance/retreat speed and opening/closing speed are set so as to gradually reach high speed.

As illustrated in FIG. 4, with the arrangement wherein the manually-driven operation unit 5 is provided on the upper portion of the main body portion 3, the programmed instruction unit 6 is provided, for example, at the left side (lower side in the drawing) as viewed from the upper direction toward the tip, and at the side face shifted 90 degrees as to the circumferential direction. The programmed instruction unit 6 is, for example, a push-to-connect type, which is a type switch to be held at the position illustrated in the solid line following being pressed. This switch is in an OFF state at the time of a protruding state illustrated in the dashed line. A pushed state illustrated in the solid line is an ON state, and in other words, a programmed-control instruction signal serving as the second instruction signal is output to the instruction-signal obtaining unit 23b of the signal input unit 23.

Note that when returning the above programmed instruction unit 6 to an ON state or OFF state, the user further subjects the programmed instruction unit 6 to a pushing-in operation once more. Also, the programmed instruction unit 6 may be a press-to-contact-type switch for returning to the original state following being pushed in.

With the present embodiment, a so-called wired type is employed by connecting between the operation instructing device 2 and the control device 20 via the signal cable 2a. However, the relation between the operation instructing device 2 and the control device 20 is not restricted to a wired type, or rather may be a wireless type such as the operation instructing device 2A illustrated in FIG. 5. With this arrangement, the operation instructing device 2A comprises, for example, a transmitter 7 within the main body portion 3, and electric supply battery 8 within the grip body 4.

Thus, the operation instructing device 2A transmits an operation instructing signal accompanying operation of the operating lever 5a, or a programmed-control instructing signal to be output from the programmed instruction unit 6 to the control device 20 via the transmitter 7 using electric power from the battery 8. In the event of this arrangement, the control device 20 is arranged so as to include a receiver (not shown) for receiving a signal to be transmitted from the transmitter 7.

Description will be made regarding the electrically-driven advance/retreat device 40 with reference to FIG. 1, FIG. 6, and FIG. 7.

The electrically-driven advance/retreat device 40 comprises two rollers 43a and 43b, which can move rotationally, within a box body 41. The box body 41 comprises a treatment-tool insertion unit 42 wherein the sheath 52 of the biopsy forceps 50 is inserted into one face side of facing faces thereof. The treatment-tool insertion unit 42 is provided with a communicating hole 42*a*. A forceps plug 42*b* made up of an elastic member is provided at the communicating hole 42*a*. A slit 42*c* into which the sheath 52 is inserted is provided at the forceps plug 42*b*. The other face side of the box body 41 is provided with a sheath inserting hole 41*a* through which the sheath 52 inserted via the slit 42*c* passes. The circumference of the sheath inserting hole 41*a* is provided with a scope fixing unit 41*b* for connecting and fixing the box body 41 to the treatment-tool attachment 12*c*. The scope fixing unit 41*b* is connected to the treatment-tool attachment 12*c* in an airtight manner.

Accordingly, for example, in a state in which the inside of the body cavity is distended by air feed by the endoscope 10 so as to readily observe the inside of the body cavity, when the sheath 52 of the biopsy forceps 50 is inserted or removed via the electrically-driven advance/retreat device 40 attached to the treatment-tool attachment 12*c*, pressure within the body cavity is prevented from deterioration.

The two rollers 43*a* and 43*b* provided within the box body 41 are each made up of a resin member having elasticity. The rollers 43*a* and 43*b* are fixed to the corresponding rotational movement shafts 43A and 43B in an integrated manner. The outer face of the sheath 52 inserted via the slit 42*c* is pressed and nipped by the respective rollers 43*a* and 43*b*. The rotational movement shaft 43A is a driving shaft, and is moved rotationally by a motor 44 disposed within the box body 41. On the other hand, the rotational movement shaft 43B is a driven shaft, and is disposed within the box body 41 so as to be moved rotationally. The motor 44 is provided with an encoder 44*a* for detecting the amount of rotation and rotational angle of the motor. The detection value of the encoder 44*a* is output to the second motor obtaining unit 23*j* of the motor rotating-speed obtaining unit 23*e* via the signal cable 40*a*.

According to this arrangement, the motor 44 is driven by a control signal being output from the second output unit 24*b* to the electrically-driven advance/retreat device 40 via the signal cable 40*a*. Subsequently, the motor 44 is driven in a state in which the sheath 52 is nipped between the rollers 43*a* and 43*b*, whereby the rotational movement shaft 43A is rotated. Then, the sheath 52 nipped between the rollers 43*a* and 43*b* advances or retreats along with rotational movement of the roller 43*a*. With the present embodiment, the CPU 21 controls driving of the motor 44 to advance or retreat the sheath 52 disposed within the treatment-tool channel 11*e* a predetermined distance.

The motor 44 is driven and controlled by the CPU 21 based on an advance signal, retreat signal to be output along with leaning operation of the operating lever 5*a*, or the operating program registered on the storage device 22.

Note that the rotational movement shafts 43A and 43B are supported so as to be moved rotationally by the side wall of the box body 41 and a support plate member 41*c* such that the rotational movement shafts 43A and 43B come in parallel with each other, and also the roller faces of the respective rollers 43*a* and 43*b* securely installed to the rotational movement shafts 43A and 43B are separated at a predetermined interval.

Figure 8:
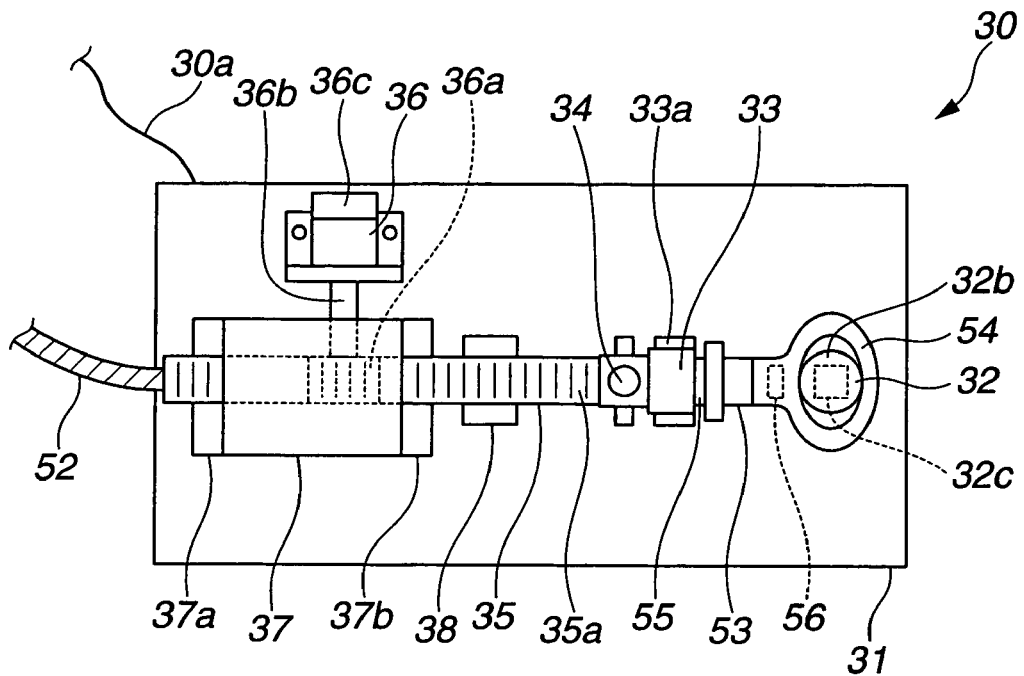
FIG. 8 is a plan view of an electrically-driven operation device in which the handle of a treatment tool is installed as viewed from above.
Figure 9:
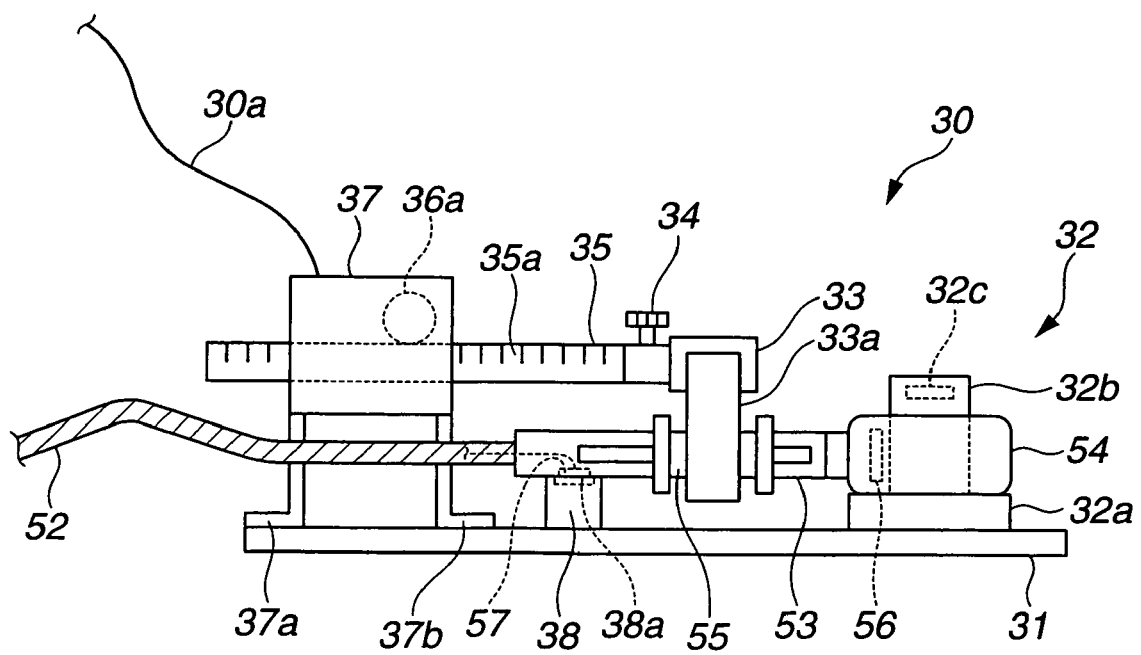
FIG. 9 is a side view of the electrically-driven operation device in which the handle of a treatment tool is installed as viewed from side.

Description will be made regarding the electrically-driven operation device 30 with reference to FIG. 1, FIG. 8, and FIG. 9.

The electrically-driven operation device 30 includes a plate-shaped base member 31. The base member 31 is securely installed with a ring-retainer portion 32, a holding box 37, and an installation portion 38. The holding box 37 is securely installed to the base member 31 via a pair of fixing members 37*a* and 37*b*. A rack 35 making up a linear cog 35*a* is held linearly in the holding box 37 so as to be advanced or retreated. A pinion gear 36*a* for gearing with the linear cog 35*a* of the rack 35 is disposed within the holding box 37. The pinion gear 36*a* is securely installed to the motor shaft 36*b* of the motor 36.

Accordingly, in a state in which the pinion gear 36*a* meshes with the linear cog 35*a* provided to the rack 35, the pinion gear 36*a* securely installed to the motor shaft 36*b* is moved rotationally, and the rack 35 advances or retreats along with rotational movement thereof. The motor 36 is provided with an encoder 36*c* for detecting the amount of rotation, and rotational angle of the motor. The detection value of the encoder 36*c* is output to the first motor obtaining unit 23*h* of the motor rotating-speed obtaining unit 23*e* via the signal cable 30*a*.

According to this arrangement, the motor 36 is driven by a control signal being output from the first output unit 24*a* to the electrically-driven operation device 30 via the signal cable 30*a*. Subsequently, the rack 35 is moved along with driving of the motor 36. Then, a slider 55 held by a slider-retainer portion 33 advances or retreats along the shaft of the handle portion 53*a* predetermined distance. With the present embodiment, the CPU 21 controls driving of the motor 36 to move the rack 35, and thus, moves the slider 55 fixed with the base portion of the operating wire to subject the tissue sampling unit 51 making up the biopsy forceps 50 to opening/closing operation.

The motor 36 is driven and controlled by the CPU 21 based on an opening signal or closing signal to be output along with leaning operation of the operating lever 5*a*, or the operating program registered on the storage device 22.

Note that one end portion of the rack 35 is arranged so as to be attached with the slider-retainer portion 33 including a holder 33*a* via a setscrew 34. The holder 33*a* making up the slider-retainer portion 33 is disposed sandwiching the slider 55 making up the handle portion 53. Specifically, the holder 33*a* holds the slider 55 so as to sandwich the body between a pair of flanges provided at the slider 55.

The ring-retainer portion 32 comprises a ring pedestal 32*a* and a protrusion 32*b*. The ring pedestal 32*a* is securely installed to the base body 31. The protrusion 32*b* is inserted and disposed into the finger-hooking ring 54 making up the handle portion 53. The protrusion 32*b* is provided with a treatment-tool information reader device (hereinafter, referred to as reader/writer) 32*c* which is an information reading unit for reading the treatment tool information registered on the IC chip 56. The reader/writer 32*c* and the IC chip 56 together make up an RFID.

The hole portion of the finger-hooking ring 54 is disposed on the protrusion 32*b*, whereby the handle portion 53 is integrally fixed and held by the electrically-driven operation device 30. At this time, the information of the IC chip 56 is read by the reader/writer 32*c*, and treatment-tool information thereof is output to the treatment-tool information obtaining unit 23*c* of the control device 20 via the signal cable 30*a*. The CPU 21 determines the presence or type of a treatment tool from the treatment-tool information output to the treatment-tool information obtaining unit 23*c*.

Upon the finger-hooking ring 54 being disposed on the protrusion 32*b* in a predetermined state, one face of the finger-hooking ring 54 comes into contact with the ring pedestal 32*a*. In this disposed state, a part of the handle portion 53 is disposed on the installation portion 38. Thus, the handle portion 53 of the biopsy forceps 50 is disposed in parallel in a state separated from the base body 31. The installation portion 38 is provided with an electric connection portion 38a to be electrically connected to the electric contact portion 57. Accordingly, the handle portion 53 is installed in the installation portion 38, thereby leading to a state in which the electric contact portion 57 and the electric connection portion 38a are electrically connected.

Thus, the pressure signal to be output from the first sensor 51c, and the closed-state signal to be output from the second sensor 51d are output to the control device 20 via a signal line (not shown), the electric contact portion 57, electric connection portion 38a, and signal cable 30a. Subsequently, the pressure signal is input to, for example, the first sensor obtaining unit 23f provided in the sensor obtaining unit 23d, and the closed-state signal is input to the second sensor obtaining unit 23g.

Note that the outside diameter dimension of the protrusion 32b making up the ring-retainer portion 32 is formed generally equal to the inside diameter of the hole portion of the finger-hooking ring 54. Accordingly, the handle portion 53 is securely held by the ring-retainer portion 32.

Also, the outside diameter dimension of the protrusion 32b of the ring-retainer portion 32 may be set to be slightly smaller than the inside diameter of the hole portion of the finger-hooking ring 54. In this case, the outer circumference of the protrusion 32b is covered with a tube body having elasticity. Thus, the handle portion 53 can be securely held by the ring-retainer portion 32.

With the endoscope system 1 thus configured, upon a surgeon leaning and operating the operating lever 5a provided in the operation instructing device 2, the first instruction signal corresponding to the leaned direction is output to the manually-driven signal processing unit 23a of the signal input unit 23 via the signal cable 2a.

That is to say, the surgeon leans and operates the operating lever 5a of the manually-driven operation unit 5 in the tip direction or base direction. Then, a sheath advance operation instructing signal for operating the sheath 52, or a retreat signal is output to the manually-driven signal processing unit 23a from the manually-driven operation unit 5. The advance signal or the retreat signal input to the manually-driven signal processing unit 23a is output to the electrically-driven advance/retreat device 40 via the second output unit 24b of the control-signal output unit 24, and the signal cable 40a as a control signal under control of the CPU 21.

Consequently, the driving side roller 43a is moved rotationally for a predetermined amount depending on the leaning operation of the operating lever 5a, and the sheath 52 which is pressed and nipped between the rollers 43a and 43b is advanced or retreated along with rotational movement thereof. Thus, the tissue sampling unit 51 advances or retreats.

On the other hand, upon the surgeon leaning and operating the operating lever 5a to the left or right direction as viewed from the upper direction toward the tip of the manually-driven operation unit 5, an opening signal or closing signal is output to the manually-driven signal processing unit 23a. The opening signal or closing signal input to the manually-driven signal processing unit 23a is output to the electrically-driven operation device 30 via the first output unit 24a of the output unit 24, and the signal cable 30a as a control signal under control of the CPU 21.

Consequently, the pinion gear 36a provided in the motor shaft 36b is moved rotationally for a predetermined amount depending on the leaning operation of the operating lever 5a. Subsequently, the rack 35 including the linear cog 35a which meshes with the pinion gear 36a advances or retreats along with rotational movement of the pinion gear 36a. Then, the slider 55 is advanced or retreated along the shaft of the handle portion 53 by the slider 55 being held by the slider-retainer portion 33 connected to the rack 35. Thus, the operating wire is advanced or retreated, and the tissue sampling unit 51 is subjected to an opening operation or closing operation.

That is to say, the surgeon can perform an operation for guiding the tissue sampling unit 51 out from the tip portion 11a side of the insertion unit 11 toward the tissue direction, and an operation for pulling back the tissue sampling unit 51 from the tissue direction side to the tip portion 11a side by leaning and operating the operating lever 5a in the tip direction or base direction. Also, the surgeon can perform an operation for making the tissue sampling unit 51 an open state, and an operation for making it a closed state by leaning the operating lever 5a in the above left direction or the above right direction.

Figure 10:
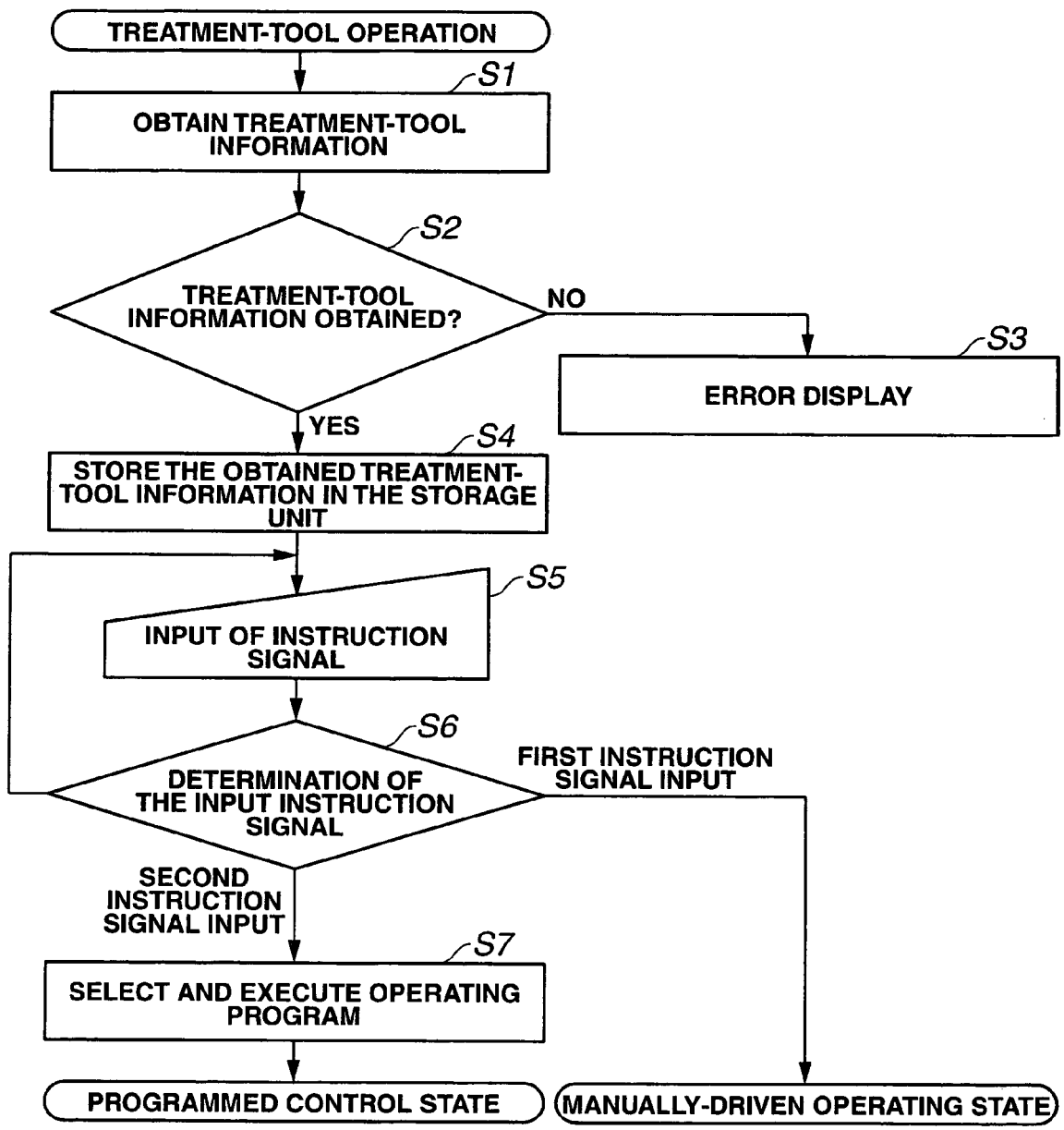
FIG. 10 is a flowchart describing a procedure for determining whether operation of a treatment tool is manually performed using a CPU, or is performed by programmed control.

A treatment-tool operation in the above endoscope system 1, as illustrated in FIG. 10 for example, is arranged so as to be selectively switched to a manually-driven operating state in which a treatment tool is operated in accordance with the surgeon's side operation of the operating lever 5a, or a programmed-control state in which a treatment tool is operated in accordance with the operating program registered beforehand.

The control device 20 of the endoscope system 1 is set to an ON state. The CPU 21 performs processing for obtaining treatment-tool information using the treatment-tool information obtaining unit 23c as shown in step S1 in FIG. 10. That is to say, the CPU 21 confirms the presence of the treatment-tool information by accessing the treatment-tool information obtaining unit 23c. In the event of obtaining no treatment-tool information in step S2, the CPU 21 proceeds to step S3, and performs processing for performing error display. On the other hand, in the event of obtaining treatment-tool information in step S2, the CPU 21 proceeds to step S4, and stores the treatment-tool information in the storage unit 21a. Thus, the control device 20 enters a state in which the type of a treatment tool has been identified.

Next, the CPU 21 monitors whether or not the instruction signal to be output from the operation instructing device 2 is input to the signal input unit 23 as shown in step S5.

When detecting input of the signal to the signal input unit 23 in step S5, the CPU 21 proceeds to step S6, and performs determination of the input instruction signal. That is to say, in step S6 the CPU 21 determines whether the instruction signal is the first instruction signal to be input to the manually-driven signal processing unit 23a, or the second instruction signal to be input to the instruction-signal obtaining unit 23b.

In the event that the CPU 21 determines in step S6 that the instruction signal is the first instruction signal, the CPU 21 enters a manually-driven operating state. Here, the CPU 21 determines whether the first instruction signal is the instruction signal corresponding to the electrically-driven operation device 30 or the instruction signal corresponding to the electrically-driven advance/retreat device 40. Subsequently, the CPU 21 outputs the control signal corresponding to the instruction signal to the electrically-driven operation device 30 from the output unit 24a, and/or outputs this to the electrically-driven advance/retreat device 40 from the output unit 24b. Thus, the tissue sampling unit 51 performs at least one of an advance/retreat operation or an opening/closing operation along with the surgeon's operation of the operating lever 5a.

In the event that the CPU 21 determines in step S6 that the instruction signal is the second instruction signal, the CPU 21 proceeds to step S7, and selects and executes the operating program to enter a programmed-control state. That is to say, in step S7 the CPU 21 accesses the storage device 22 to select the operating program corresponding to the treatment-tool information stored in the storage unit 21a of the programs registered on the storage device 22, and executes the selected program to operate a treatment tool.

With the present embodiment, a biopsy-forceps operating program for operating the biopsy forceps 50 is executed. Thus, the CPU 21 outputs the control signal in accordance with the program to the electrically-driven operation device 30 or/and the electrically-driven advance/retreat device 40 from the output units 24a and 24b. Thus, the tissue sampling unit 51 performs an advance/retreat operation and an opening/closing operation based on the program.

Note that in a programmed-control state in which the program registered on the storage device 22 is executed, in the event that the operating lever 5a provided on the manually-driven operation unit 5 of the operation instructing device 2 is leaned and operated, all first instruction signals to be input to the manually-driven signal processing unit 23a from the operation instructing device 2 are cancelled. In other words, the operating lever 5a loses function thereof at the time of a state in which the programmed instruction unit 6 is pressed and operated to the solid line position in FIG. 4 or the like. That is to say, in a programmed-control state, even in the event of a medical worker accidentally touching the operating lever 5a, an advance/retreat operation and an opening/closing operation by the program is performed.

Also, in the event of simultaneously confirming input of the first instruction signal and input of the second instruction signal in step S6, the CPU 21 determines those as erroneous operations, cancels the first instruction signal and the second instruction signal, and proceeds to step S5.

Further, in a programmed-control state, upon the surgeon turning off the programmed instruction unit 6, the CPU 21 immediately stops the programmed-control state.

Description will be made more specifically regarding operations of the endoscope system 1 thus configured.

First, when using the endoscope system 1 in surgery, a medical staff (hereinafter, referred to as staff) attaches a treatment tool to be used for surgery, for example, the handle portion 53 of the biopsy forceps 50 to the electrically-driven operation device 30 (see FIG. 8 and FIG. 9). At this time, the staff mounts the slider-retainer portion 33 removed from the rack 35 onto the slider 55 making up the handle portion 53 of the biopsy forceps 50. Subsequently, the staff disposes the finger-hooking ring 54 of the handle portion 53 in the ring-retainer portion 32. At this time, the staff inserts the finger-hooking ring 54 until one face of the finger-hooking ring 54 in contact on the ring pedestal 32a of the ring-retainer portion 32, and also makes the transition to a state in which a part of the handle portion 53 is mounted on the installation portion 38. Subsequently, as illustrated in FIG. 9, the staff connects the slider-retainer portion 33 and the rack 35 using the set-screw 34.

Figure 6:
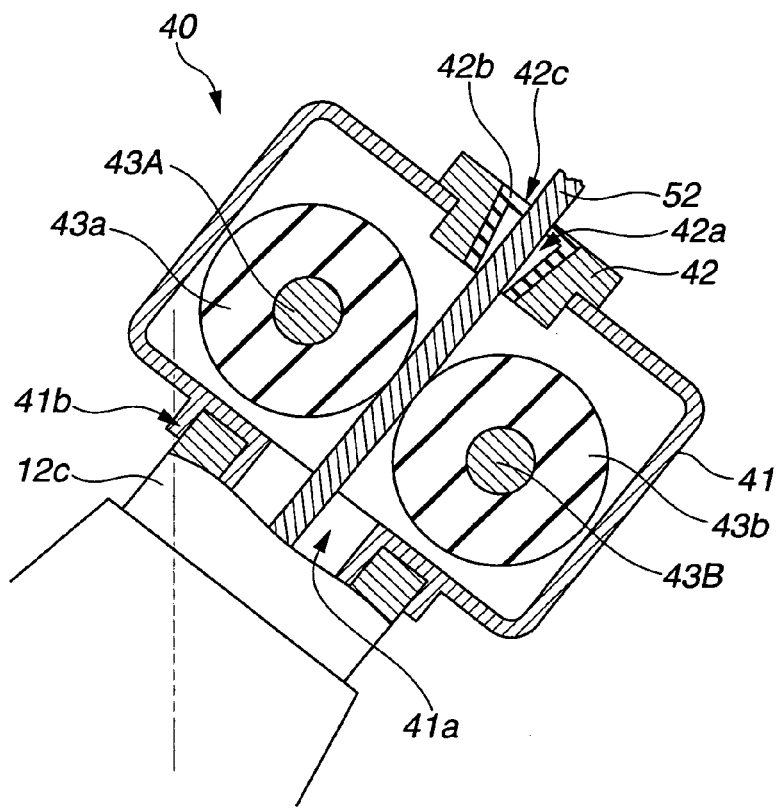
FIG. 6 is a cross-sectional view in the vertical direction illustrating the internal configuration of an electrically-driven advance/retreat device.
Figure 7:
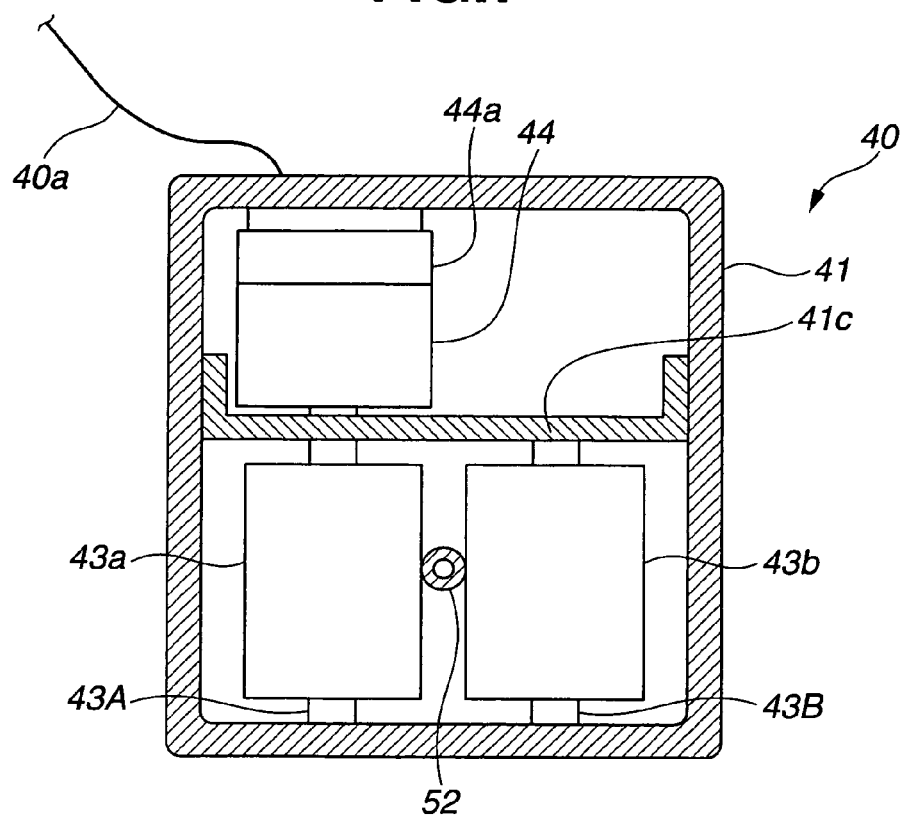
FIG. 7 is a cross-sectional view in the lateral direction illustrating the internal configuration of the electrically-driven advance/retreat device.

Also, the staff mounts the electrically-driven advance/retreat device 40 on the treatment-tool attachment 12c of the endoscope 10 (see FIG. 6). Subsequently, the staff inserts the sheath 52 of the biopsy forceps 50 into the treatment-tool channel 11e of the endoscope 10 via the electrically-driven advance/retreat device 40 and the treatment-tool opening 12b. Thus, the sheath 52 of the biopsy forceps 50 is in a state of being pressed and nipped between the two rollers 43a and 43b.

Next, the staff connects the signal cable 2a extended from the operation instructing device 2 to the control device 20, and also connects the universal cord 13 and the signal cables 30a and 40a to the control device 20.

Following preparation being completed, the medical staff first turns the power of the control device 20 to an ON state. Then, the treatment-tool information registered on the IC chip 56 provided in the handle portion 53 is read by the reader/writer 32c provided in the protrusion 32b, and is output to the treatment-tool information obtaining unit 23c. Then, the CPU 21 stores the treatment-tool information that the treatment tool is the biopsy forceps 50 in the storage unit 21a, and monitors input of an instruction signal.

Figure 11:
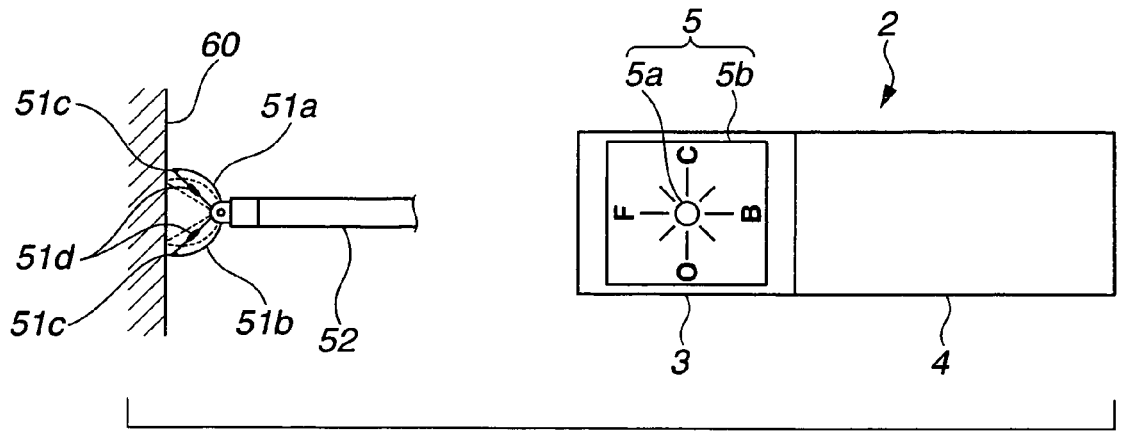
FIG. 11 is a diagram describing a state when determination is made regarding whether to operate a biopsy forceps manually or by programmed control.

Next, the surgeon inserts the insertion unit 11 of the endoscope 10 toward a target portion within the body cavity of a subject while observing an endoscope image. Subsequently, the surgeon performs an insertion operation, and a bending operation for bending the bending portion 11b, and so forth while observing an endoscope image on the screen, and confronts the tip portion 11a of the insertion unit 11 with the tissue of the target portion so as to facilitate treatment. Subsequently, the surgeon moves and operates the tissue sampling unit 51 disposed in the vicinity of the treatment-tool opening 12b by leaning and operating the operating lever 5a so as to protrude the tissue sampling unit 51 from the tip face of the tip portion 11a of the endoscope, and also performs an operation for confronting the tissue sampling unit 51 of the biopsy forceps 50 with the vicinity of tissue 60 as illustrated in FIG. 11. Subsequently, the surgeon selects whether to perform sampling of tissues by manually operating the biopsy forceps 50 while observing an endoscope image, or perform sampling of tissues by operating the biopsy forceps 50 under programmed control.

In the event of manually operating the biopsy forceps 50, the surgeon operates the operating lever 5a of the operation instructing device 2 illustrated in FIG. 2 as appropriate. Then, the first instruction signal corresponding to the surgeon's side operation is output to the manually-driven signal processing unit 23a from the manually-driven operation unit 5. Thus, the tissue sampling unit 51 is advanced, opened, closed, or retreated depending on the surgeon's side operation, whereby sampling of tissue can be performed.

Figure 12:
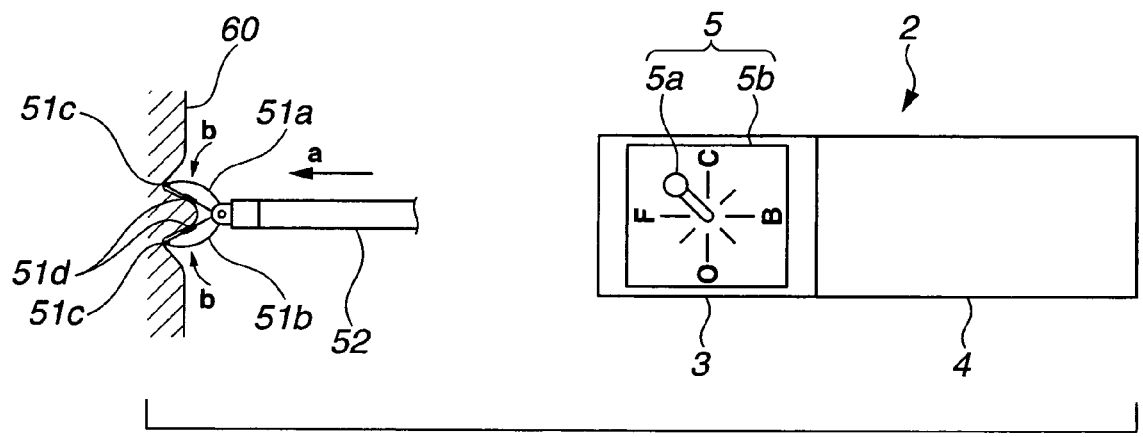
FIG. 12 is a diagram describing a state in which a biopsy forceps is operated by leaning the operating lever of the operation instructing device in an intermediate region between advancement and closing operation.

Now, the surgeon leans the operating lever 5a of the operation instructing device 2, for example, to an area between the reference mark "F" and reference mark "C", as illustrated in FIG. 12. Then, the tissue sampling unit 51 performs an operation for advancing toward the tissue 60 as illustrated in the arrow a, and also performs an operation for closing as illustrated in the arrow b. In other words, the tissue sampling unit 51 can perform sampling of the tissue 60 by changing the tissue sampling unit 51 from an open state to a closed state while moving toward the tissue by the surgeon leaning and operating the operating lever 5a to an area between the reference mark "F" and reference mark "C", as illustrated in the drawing.

Also, the pressure value calculated from the pressure signal to be output from the first sensor 51c is arranged so as to be displayed on an unshown display panel included in the control device 20. Also, when a closed-state detection signal is output from the second sensor 51d, for example, a sampling-state notification lamp (not shown) included in the control device 20 is arranged to change from a blinking state to a lit state so as to notify that the tissue sampling unit 51 is in a closed state.

Figure 13:
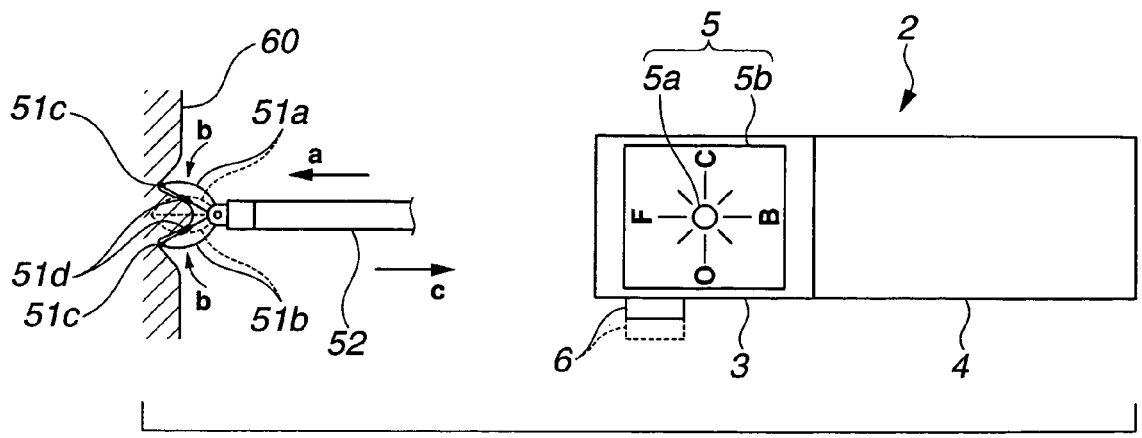
FIG. 13 is a diagram describing a state in which a biopsy forceps is operated in a programmed-control state by the biopsy-forceps program illustrated in FIG. 14.

On the other hand, in the event of operating the biopsy forceps 50 by programmed control to perform sampling of tissue, the surgeon confronts the tissue sampling unit 51 of the biopsy forceps 50 with the vicinity of the tissue 60 as illustrated in FIG. 11, following which sets the tissue sampling unit 51 to a desired open state, and pushes in and operates the programmed instruction unit 6 such as illustrated in FIG. 13. Then, the second instruction signal is output from the manually-driven operation unit 5 to the instruction-signal obtaining unit 23b. Subsequently, as shown in the above steps S5 through S7, the tissue sampling unit 51 enters a programmed-control state of being operated based on the biopsy-forceps program registered on the storage device 22.

Now, description will be made regarding one example of sampling tissue using the biopsy-forceps program with reference to FIG. 13 and FIG. 14.

In a programmed-control state, the CPU 21 first performs origin processing for setting the point where the programmed instruction unit 6 is pushed in and operated, to a treatment-start point-of-origin, such as shown in step S111. That is to say, in the surgeon's desired open state, the CPU 21 identifies the position of the tissue sampling unit 51 stopped at the desired position, and so registers the detection value of the encoder 36c which is the positional information of the motor 44 in the storage unit 21a as the origin. At this time, the CPU 21 registers the distance moved from the vicinity of the treatment-tool opening 12b to the treatment start origin as a removal distance.

Subsequently, the CPU 21 performs control for advancing the tissue sampling unit 51 while keeping the open state of the tissue sampling unit 51, as shown in step S12. That is to say, the CPU 21 outputs a control signal for keeping the open state of the tissue sampling unit 51 to the electrically-driven operation device 30 from the first output unit 24a. Also, the CPU 21 outputs a control signal for advancing the tissue sampling unit 51 in the arrow a direction toward the tissue 60 at a predetermined speed to the electrically-driven advance/retreat device 40 from the second output unit 24b. Then, the tissue sampling unit 51 advances toward the tissue along with rotation of the motor 44, and a detection value to be output from the encoder 44a is consecutively input to the second motor obtaining unit 23j in accordance with advancement thereof.

As shown in step S13, the CPU 21 subjects the pressure signal value, which is output from the first sensor 51c by the tissue sampling unit 51 being in contact with the tissue 60, and is consecutively input to the first sensor obtaining unit 23f, to computing processing at the computing processing unit 21b to obtain this as a pressing pressure value following outputting the control signal for instructing advancement. Subsequently, the CPU 21 outputs pressing pressure value thereof to the determining unit 21c, and compares and determines whether or not the pressing pressure value has reached the most appropriate tissue sampling pressure P which is set within the program at the time of sampling tissue.

Subsequently, when determining in step S13 that the pressing pressure value has reached the sampling start pressure P, the CPU 21 performs the processing in step S14.

In step S14, the CPU 21 extracts the detection value of the encoder 44a, which indicates the amount of rotation of the motor 44 at the time of the tissue sampling unit 51 being in contact with the tissue 60, from the second motor obtaining unit 23j to register this on the storage unit 21a. The CPU 21 obtains the difference between the detection value of the encoder 44a registered on the storage unit 21a and the detection value of the encoder 44a registered this time to calculate the movement distance from the origin of the tissue sampling unit 51 to the tissue, and registers this as the amount of return.

In step S15, the CPU 21 performs control for causing the tissue sampling unit 51 to perform a closing operation. Specifically, the CPU 21 performs control for stopping advancement of the tissue sampling unit 51, and control for causing the biopsy cups 51a and 51b to perform a closing operation in the arrow b direction at the most appropriate speed for sampling of tissue.

That is to say, the CPU 21 outputs a control signal for stopping advancement of the tissue sampling unit 51 to the electrically-driven advance/retreat device 40 from the second output unit 24b. Also, the CPU 21 outputs a control signal for closing the biopsy cups 51a and 51b at the most appropriate predetermined speed for sampling of tissue to the electrically-driven operation device 30 from the first output unit 24a.

Subsequently, the CPU 21 determines in step S16 whether or not the tissue sampling unit 51 in an open state illustrated in the solid line in FIG. 13 has changed to a closed state as illustrated by the dashed line. That is to say, the CPU 21 monitors whether or not the closed-state signal to be output from the second sensor 51d is input to the second sensor obtaining unit 23f.

Subsequently, upon the cups making up the tissue sampling unit 51, which is subjected to a closing operation, coming into contact with each other, a closed-state signal is output to the second obtaining unit 23g from the second sensor 51d provided in the tissue sampling unit 51, and the open-state signal is input to the second sensor obtaining unit 23g. Then, the CPU 21 determines that the tissue sampling unit 51 has changed into a closed state, and proceeds to step S17.

In step S17, the CPU 21 performs control for keeping the tissue sampling unit 51 in a closed state, and control for retreating the tissue sampling unit 51 in the arrow c direction at a predetermined speed. That is to say, the CPU 21 outputs a control signal for keeping the tissue sampling unit 51 in a closed state to the electrically-driven operation device 30 from the first output unit 24a. Also, the CPU 21 retreats the tissue sampling unit 51 in the arrow c direction only for the above amount of return at a predetermined speed to the electrically-driven advance/retreat device 40 from the second output unit 24b, following which outputs a control signal for further retreating the tissue sampling unit 51 only the removal distance from the origin.

Thus, the tissue sampling unit 51, which has performed sampling of tissue, and is kept in a closed state, starts movement toward the arrow c direction, retreats to the vicinity of the treatment-tool opening 12b via the treatment-tool channel 11e from the tip opening 11d, and stops. That is to say, a programmed-control state by the biopsy-forceps program ends. Here, the surgeon turns off the programmed instruction unit 6 to cancel a programmed-control state.

Subsequently, the surgeon or staff extracts the tissue sampling unit 51 from the treatment-tool opening 12b to collect the tissue sampled at the tissue sampling unit 51.

Thus, the endoscope system principally comprises the operation instructing device, endoscope, control device, electrically-driven operation device, and electrically-driven advance/retreat device. A treatment-tool operating program for causing a treatment tool to be mounted on the electrically-driven advance/retreat device to perform the corresponding treatment operation is registered on the storage device of the control device, and also the manually-driven operation instructing unit and a programmed operation instructing unit are provided in the operation instructing device. Thus, a surgeon can selectively perform a manually-driven treatment operation and a programmed-driven treatment operation regarding operation of a treatment tool to be mounted on the electrically-driven advance/retreat device as appropriate.

Also, the surgeon operates the programmed operation instructing unit, and the tissue sampling unit of a treatment tool is controlled and operated by the biopsy-forceps program, whereby even a physician who is inexperienced in treatment can perform sampling of tissue by making the biopsy cups into a closed state while pressing biopsy cups against tissue with the appropriate amount of force, as with a physician who is experienced in treatment.

Further, the biopsy-forceps program determines whether or not the pressing pressure caused by the advancing tissue sampling unit coming into in contact with tissue has reached the sampling start pressure P to output a control signal for switching the biopsy cups from an open state to a closed state. Accordingly, sampling of tissue can be performed in a closed state of the biopsy cups, in a sure manner.

Also, the biopsy-forceps program confirms that the biopsy cups are in a closed state, following which retreats the tissue sampling unit. Accordingly, sampling of tissue by the biopsy cups can be performed in a sure manner.

Also, the encoder is provided in the motor, whereby a rotational state of the motor can be calculated at the computing processing unit. Accordingly, sampling of tissue can be performed more effectively by the CPU comparing the rotational state calculated and obtained with the value provided on the program.

Figure 14:
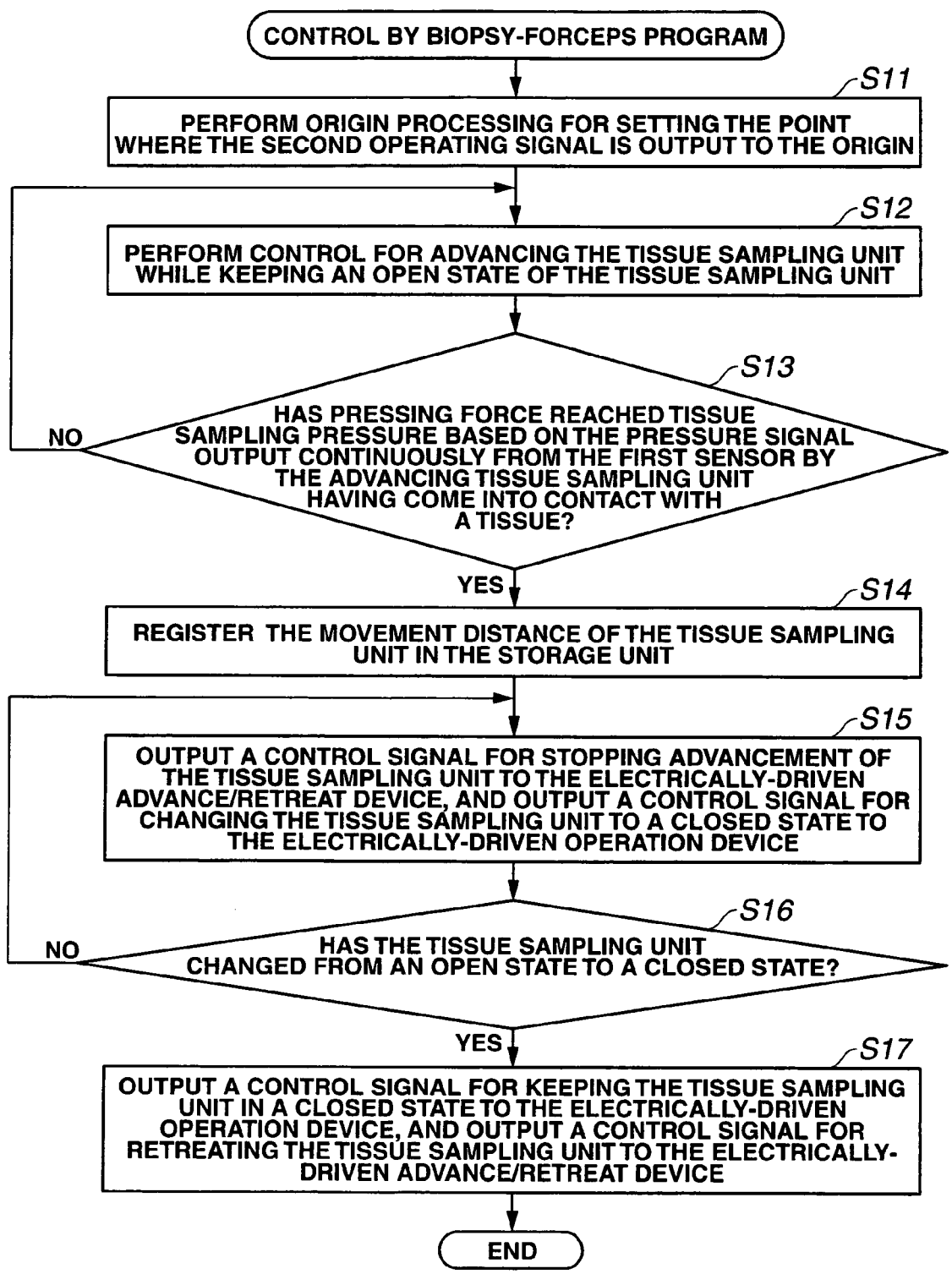
FIG. 14 is a diagram describing one control example by the biopsy-forceps program.
Figure 15:
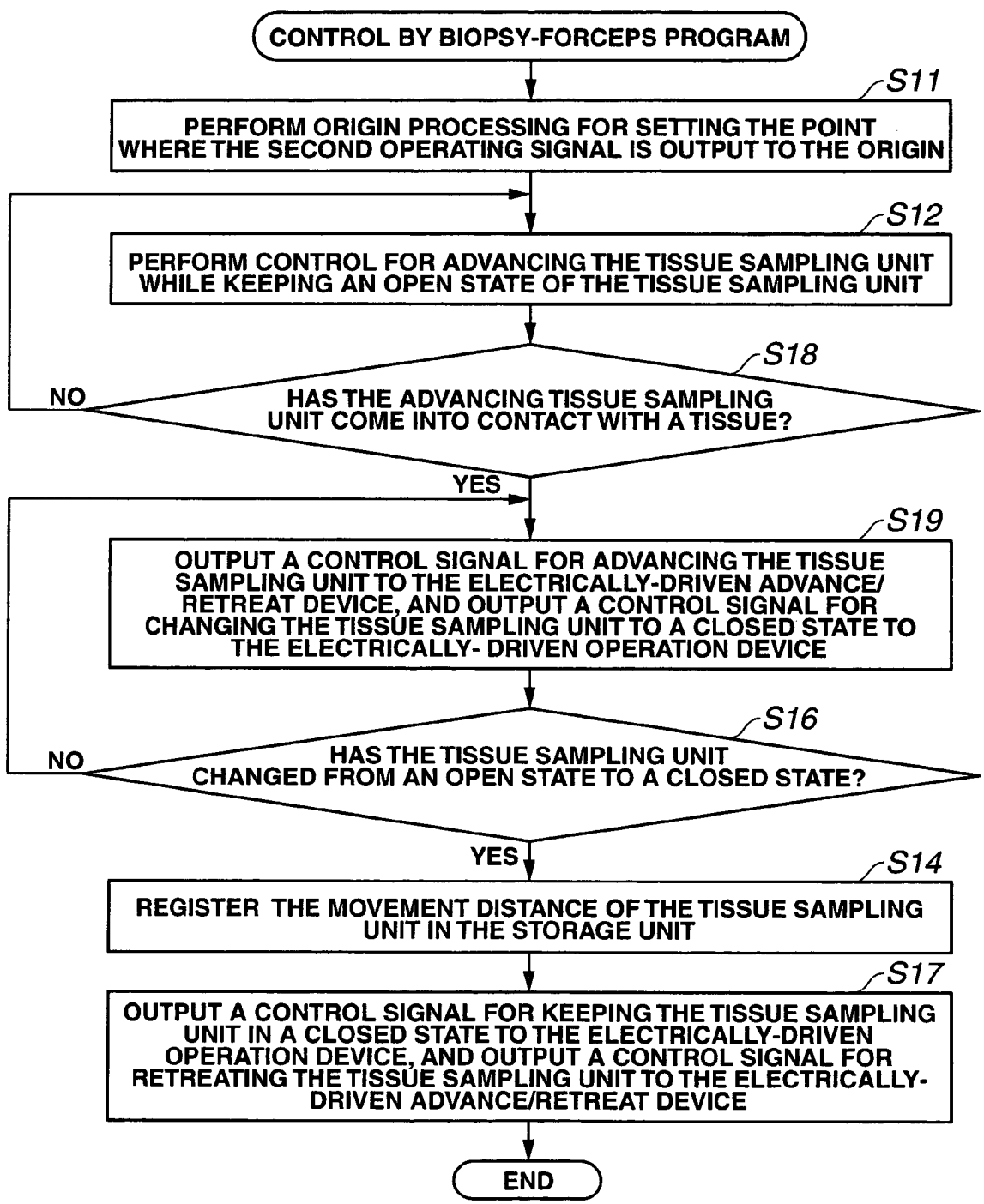
FIG. 15 is a diagram describing another control example of the biopsy-forceps program.
Figure 16:
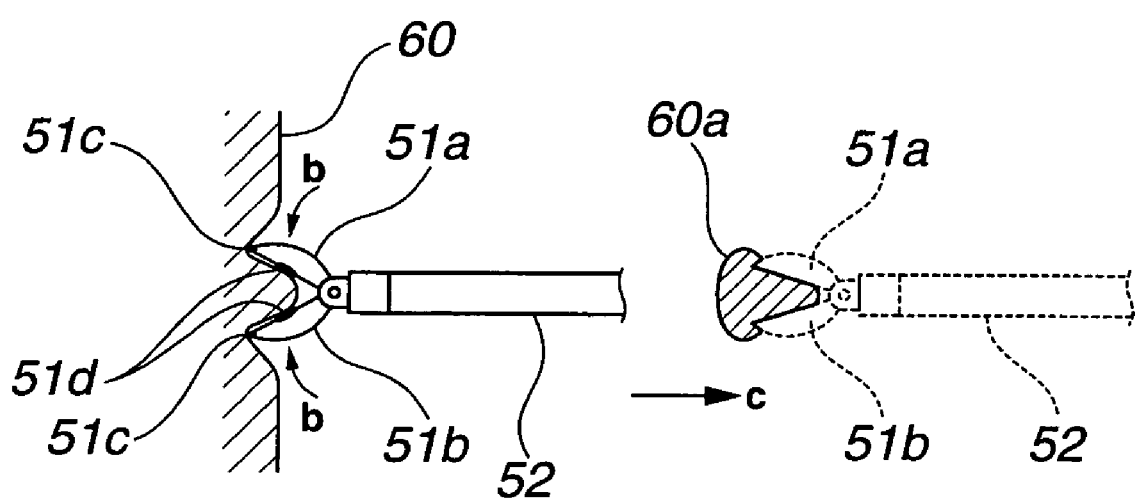
FIG. 16 is a diagram describing operation of a tissue sampling unit at the time of programmed control of a biopsy forceps in the event that a second sensor is a tissue pressure-force detection sensor.

Note that the biopsy-forceps program is not restricted to that illustrated in FIG. 14, but rather programmed control such as shown in FIG. 15 may be employed, for example. Control of sampling of tissue by the biopsy-forceps program will be described with reference to FIG. 15. In FIG. 15, the same steps as those in FIG. 14 are appended with the same step numbers to simplify description thereof.

In a programmed-control state, the CPU 21 first performs origin processing in step S11, as with the above programmed control. Subsequently, the CPU 21 performs control for advancing the tissue sampling unit 51 while keeping the open state of the tissue sampling unit 51, as shown in step S112. Thus, the tissue control unit 51 advances toward the tissue along with rotation of the motor 44, and the detection value to be output from the encoder 44a is consecutively input to the second motor obtaining unit 23j.

The CPU 21 determines whether or not the tissue sampling unit 51 is in contact with the tissue 60 as shown in step S18 following outputting a control signal for instructing advancement. That is to say, the CPU 21 monitors whether or not the pressure signal to be output from the first sensor 51c is input to the first sensor obtaining unit 23f. Subsequently, when the pressure signal to be output from the first sensor 51c is input to the first sensor obtaining unit 23f, the CPU 21 determines that the tissue sampling unit 51 is in contact with the tissue 60, and proceeds to step S119.

In step S19, the CPU 21 performs control for advancing the tissue sampling unit 51 in the arrow a direction, and control for causing the biopsy cups 51a and 51b to perform a closing operation in the arrow b direction at the most appropriate speed for sampling of tissue. Specifically, the CPU 21 detects a pressure signal, following which outputs a control signal for advancing the tissue sampling unit 51 at a predetermined speed only for a predetermined distance to the electrically-driven advance/retreat device 40 from the second output unit 24b. Also, the CPU 21 outputs a control signal for closing the biopsy cups 51a and 51b at the most appropriate predetermined speed for sampling tissue to the electrically-driven operation device 30 from the first output unit 24a. Thus, in a state in which the tissue sampling unit 51 advances, the biopsy cups 51a and 51b are changed into a closed state.

Subsequently, the CPU 21 determines in step S116 whether or not the tissue sampling unit 51 in an open state illustrated with the solid line in FIG. 13 has been changed into a closed state illustrated with the dashed line. Then, upon the cups making up the tissue sampling unit 51, which is subjected to a closing operation, coming into contact with each other, the CPU 21 determines that the tissue sampling unit 51 has been changed into a closed state, and proceeds to step S17 via step S14.

Note that following the tissue sampling unit 51 being in contact with the tissue, upon determining that the tissue sampling unit 51 has advanced a predetermined distance based on the detection value of the encoder 44a indicating the amount of rotation of the motor 44, the CPU 21 stops driving of the motor 44. Subsequently, as shown in step S14, the CPU 21 calculates the movement distance from the origin of the tissue sampling unit 51, and registers this as the amount of return.

In step S17, the CPU 21 performs control for keeping the tissue sampling unit 51 in a closed state, and control for retreating the tissue sampling unit 51 in the arrow c direction at a predetermined speed. Thus, the tissue sampling unit 51 kept in a closed state starts movement toward the arrow c direction, and is inserted into the treatment-tool channel 11e from the tip opening 11d, following which is retreated to the vicinity of the treatment-tool opening 12b, and stops. The same operations and advantages as the control program illustrated in FIG. 14 can be obtained.

With the above programmed control, an arrangement has been made wherein the tissue sampling unit 51 of the biopsy forceps 50 is confronted with the vicinity of the tissue 60 such as illustrated in FIG. 11, following which a surgeon sets the tissue sampling unit 51 to a desired open state, and pushes in and operates the programmed instruction unit 6. However, as illustrated in FIG. 11, an arrangement may be made wherein in a state in which the tissue sampling unit 51 is set to a desired open state, a surgeon presses the tissue sampling unit 51 against the tissue 60, following which the surgeon pushes in and operates the programmed instruction unit 6 to set to a programmed-control state. In this case, the CPU 21 performs control from step S14 in FIG. 14, or control from the step S119 in FIG. 15. Even with this programmed control, as with the above control program, the sensor detects that the tissue sampling unit has changed from an open state to a closed state. However, instead of providing the sensor in the forceps, programmed control may be employed wherein a control signal for operating the tissue sampling unit from an open state to a closed state only for a predetermined amount is output from the electrically-driven operation device.

Also, with the present embodiment, the second sensor 51d is a closed-state detection sensor for outputting a closed-state signal at the time of a state in which the biopsy cups 51a and 51b are closed. However, the second sensor 51d is not restricted to a closed-state detection sensor, and a tissue compressed-force detection sensor (hereinafter, referred to as compressed sensor) may be employed for detecting compressed force applied to the tissue held between the biopsy cup 51a and the biopsy cup 51b, and outputting compressed force thereof as an electric signal.

In the event that sampling of tissue is performed at the tissue sampling unit 51 in which a compressed sensor is provided as the second sensor 51d, for example, under control of the CPU 21 such as shown in step S15 in FIG. 14, the biopsy cups 51a and 51b are closed and operated at the most appropriate speed for sampling of tissue. Then, as illustrated in FIG. 13, the tissue is held between the biopsy cups 51a and 51b, following which an electric signal is output to the second sensor obtaining unit 23g from the compressed sensor serving as the second sensor.

With this arrangement, the CPU 21 outputs an electric signal to be output from the second sensor 51d and to be input consecutively to the second sensor obtaining unit 23f to the computing processing unit 21b, and performs computing processing to obtain compressed pressure instead of monitoring whether or not the closed-state signal to be output from the second sensor 51d is input to the second sensor obtaining unit 23f in step S16.

Subsequently, the CPU 21 outputs compressed pressure value thereof to the determining unit 21c to compare and determine at the determining unit 21c whether or not the compressed pressure value has reached the most appropriate tissue sampling start pressure registered on the program at the time of performing sampling of tissue. Upon determining that the compressed pressure value has reached the tissue sampling start pressure, the CPU 21 performs control for collecting tissue in the tissue sampling unit 51. That is to say, in the state illustrated with the solid line in FIG. 16, the CPU 21 outputs a control signal for retreating the tissue sampling unit 51 in the arrow c direction only for a predetermined distance at a predetermined speed to the electrically-driven operation device 30 from the first output unit 24a. Then, the tissue sampling unit 51 is moved in a state of holding the tissue, and a tissue piece 60a is sampled by the biopsy cups 51a and 51b such as illustrated in the dashed line. Subsequently, the CPU 21 proceeds to step S17, retreats the tissue sampling unit 51 in a closed state to the vicinity of the treatment-tool opening 12b, and ends control by the biopsy-forceps operating program.

The tissue sampling start pressure is a value to be set within the program, and also is a value which can be set and modified using an operating panel. Also, with the present embodiment, the tissue sampling unit 51 is provided with the first sensor 51c and the second sensor 51d. However, an arrangement may be made wherein only the second sensor 51d serving as a compressed sensor is provided in the biopsy cups 51a and 51b making up the tissue sampling unit 51.

With this arrangement, the placement position of the compressed sensor is taken into consideration. That is to say, the compressed sensor is disposed so as to obtain contact pressure at the time of advancing, and compressed pressure at the time of a closing operation. Thus, the number of sensors to be provided in the tissue sampling unit 51 is one type, whereby reduction in cost and so forth can be realized.

In the event of employing the second sensor 51d as a compressed sensor, the CPU 21 performs the origin processing in the advance/retreat direction in step S111, and also obtains the amount of opening in an open state which is set by the surgeon. This amount of opening is obtained as follows under control of the CPU 21.

First, the CPU 21 outputs a control signal for changing the tissue sampling unit 51 in an open state which is set by the surgeon into a closed state. Next, the CPU 21 obtains the amount of rotation of the motor 36 until an electric signal is output from the compressed sensor. That is to say, the CPU 21 performs subtraction between the detection value of the encoder 36c output when changing an open state to a closed state and the above detection value to obtain the amount of opening, and registers this on the storage unit 21a. Subsequently, the CPU 21 outputs a control signal for changing the tissue sampling unit 51 into an open state only for the amount of opening registered on the storage unit 21a to the electrically-driven operation device 30 from the first output unit 24a. Thus, the tissue sampling unit 51 returns to the surgeon's desired open state again.

When determining that the above compressed pressure value has reached the tissue sampling start pressure, the CPU 21 determines whether or not the open state of the tissue sampling unit is the amount of closing appropriate for sampling of tissue by obtaining the above amount of opening. Thus, in the event of determining that the amount of closing is appropriate for sampling of tissue, the CPU 21 outputs a control signal for sampling tissue at the tissue sampling unit 51. On the other hand, in the event of determining that the amount of closing is not appropriate for sampling of tissue, the CPU 21 outputs a control signal for informing the surgeon to that effect. Thus, a problem wherein no tissue is sampled in the tissue sampling unit 51 is prevented.

Further, advancing speed, retreating speed, cup opening speed, cup closing speed, tissue sampling pressure, and so forth at the time of causing the tissue sampling unit to perform an advance/retreat operation or an opening/closing operation by programmed control can be set or modified using an unshown operating panel provided in the control device. Thus, the surgeon can perform target treatment by operating the tissue sampling unit in a desired manner at the time of programmed control.

Also, with the present embodiment, an arrangement has been made wherein treatment-tool information is registered on, for example, a non-contact IC chip, the treatment-tool information registered on the IC chip is read out by the treatment-tool information reading device, and the treatment-tool information is output to the treatment-tool information obtaining unit. However, an arrangement may be made wherein treatment-tool information is input at, for example, the operating panel provided on the control device, and is output to the treatment-tool information obtaining unit.

With the above endoscope system 1, a treatment tool is taken as the biopsy forceps 50. However, a treatment tool is not restricted to the biopsy forceps 50, rather, various types of treatment tool such as a high-frequency snare, basket forceps, injector, marking device, and so forth can be operated by programmed control.

Hereinafter, an operation example wherein other treatment tools are programmed control by an operating program will be described for each treatment tool with reference to FIG. 17 through FIG. 35.

First, a programmed control example at the time of performing treatment for excising an affected portion such as a polyp or the like using a high-frequency snare will be described with reference to FIG. 17 through FIG. 19.

With the endoscope system 1A illustrated in FIG. 17, a treatment tool is a high-frequency snare 50A, and includes a high-frequency power supply device 70. The high-frequency power supply device 70 supplies a high-frequency current to the high-frequency snare 50A.

The handle portion 53 of the high-frequency snare 50A is set to the electrically-driven operation device 30, as described above. When the handle portion 53 is set to the electrically-driven operation device 30, the information of the IC chip 56 provided in the handle portion 53 is read by the reader/writer 32c, and is output to the treatment-tool information obtaining unit 23c of the signal input unit 23. With the high-frequency snare 50A also, the slider 55 making up the handle portion 53 is advanced or retreated along the axis of the handle portion 53, as with the above embodiment. With the high-frequency snare 50A, upon the slider 55 being advanced, a snare portion 51A serving as a function unit is guided out from the tip of the sheath 52. At this time, the snare portion 51A forms a loop shape. On the other hand, in such a state, when the slider 55 is retreated, the loop-shaped snare portion 51A is stored within the sheath 52.

The slider 55 of the high-frequency snare 50A to be employed for the present embodiment is detachably provided with one end portion of a high-frequency wiring cord 70a. The other end portion of the high-frequency wiring cord 70a is connected to the high-frequency power supply device 70. The high-frequency wiring cord 70a is connected to an unshown metal operating wire disposed within the sheath 52 via the slider 55, and is placed in an electrically connected state with the snare portion 51A. The high-frequency power supply device 70 is connected with a foot switch 71. A high-frequency current is supplied to the snare portion 51A by the surgeon operating the foot switch 71 as appropriate. That is to say, in a state in which the root portion of an affected portion is fastened by the snare portion 51A of the high-frequency snare 50A, the surgeon operates the foot switch 71, whereby a high-frequency current is supplied to the snare portion 51A, and excision of the affected portion is performed.

With the endoscope system 1A wherein the handle portion 53 of the high-frequency snare 50A is disposed in the electrically-driven operation device 30, the surgeon pushes in and operates the programmed instruction unit 6 provided in the operation instructing device 2, thereby activating a high-frequency snare operating program. In a programmed-control state, the operating lever 5a according to the present embodiment loses a function as the operating lever 5a, and also a function as a selection switch.

Figure 18A:
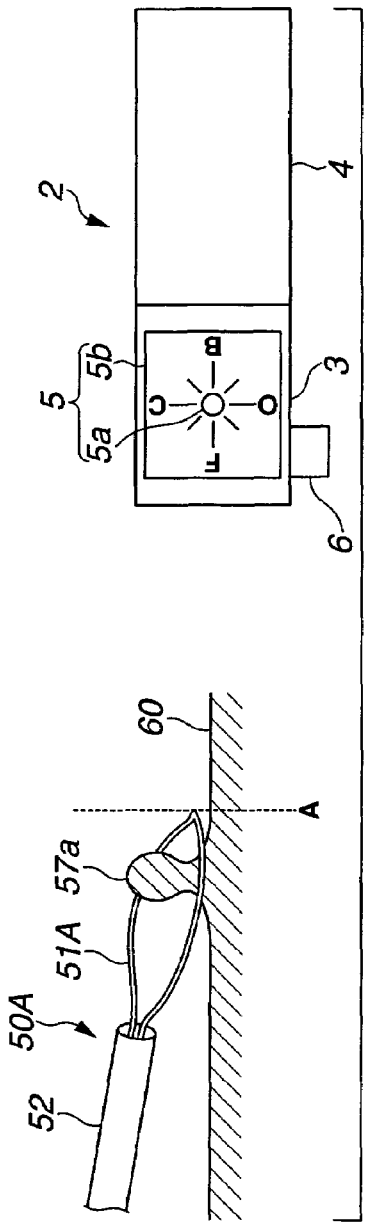
FIG. 18A is a diagram describing a state when determination is made regarding whether to operate a high-frequency snare manually or by programmed control.

Specifically, the surgeon performs the surgeon's side operation of the operating lever 5a to dispose the loop-shaped snare portion 51A in an affected portion 57a positioned at the tissue 60 within a body cavity, as illustrated in FIG. 18A. Here, in the event of desiring an operation by programmed control, the surgeon pushes in and operates the programmed instruction unit 6 provided in the operation instructing device 2. Thus, as shown in steps S4 through S7 in FIG. 10, the CPU 21 selects and executes the high-frequency snare program registered on the storage device 22 to enter a programmed-control state.

Figure 19:
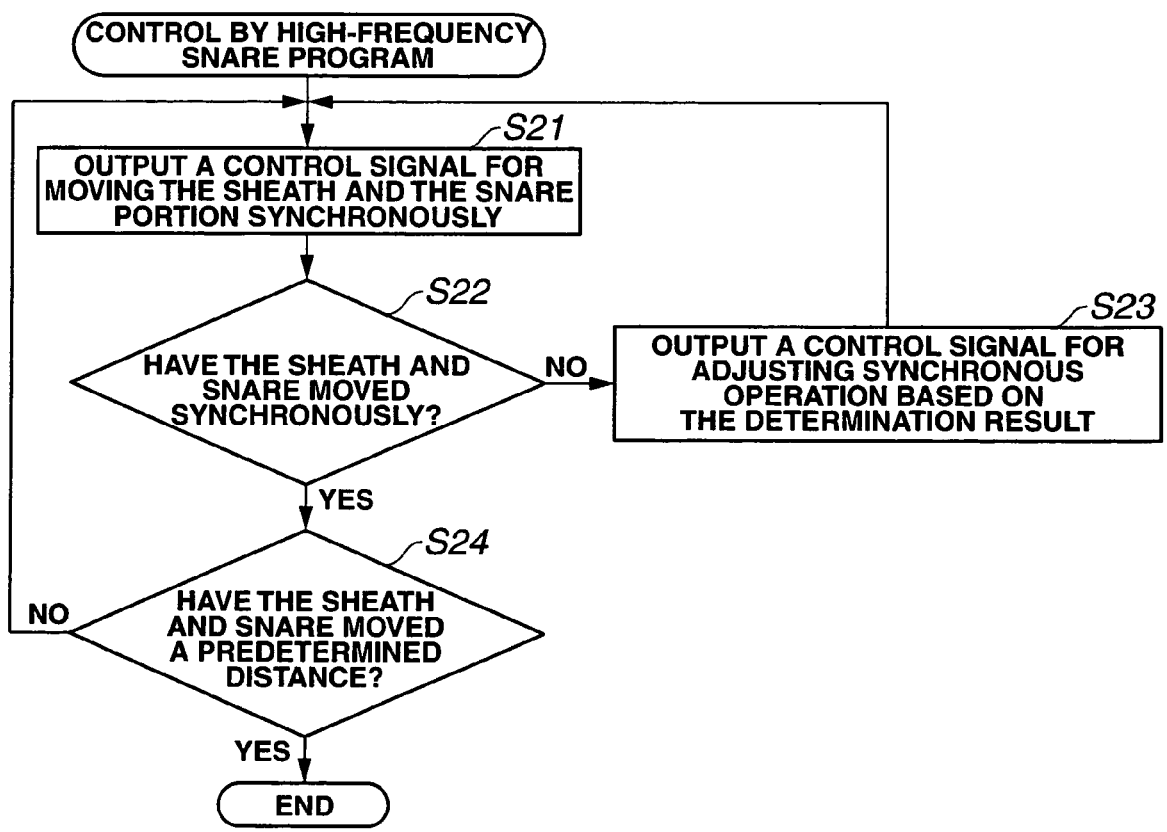
FIG. 19 is a diagram describing a control example using a high-frequency snare program.
Figure 21A:
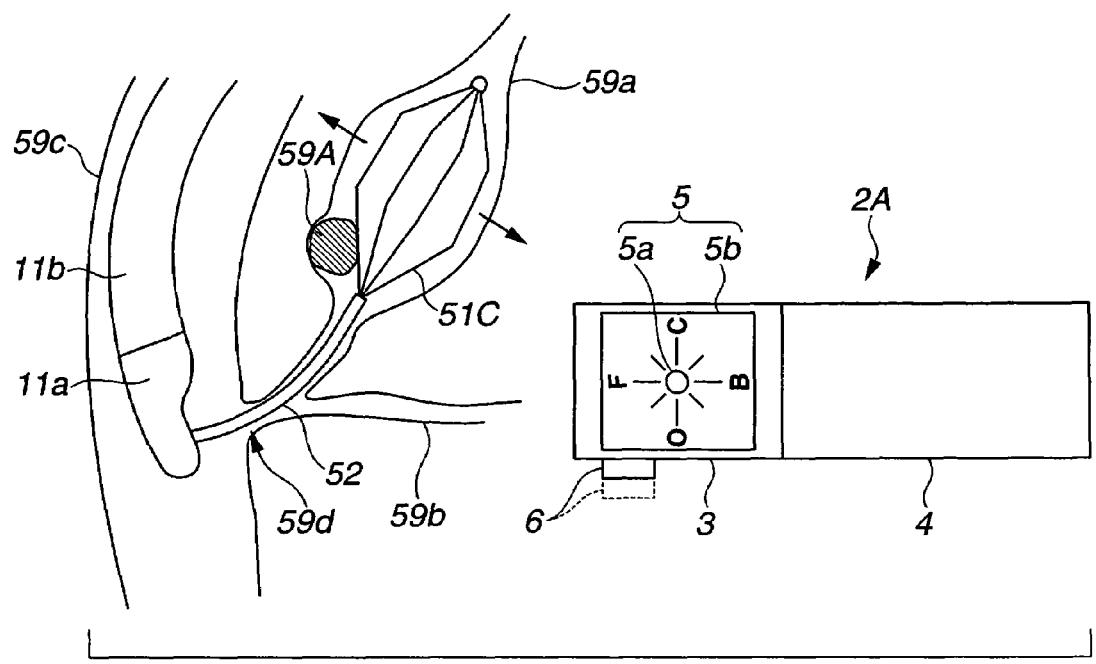
FIG. 21A is a diagram describing a state when determination is made regarding whether to operate a basket forceps manually or by programmed control.
Figure 21B:
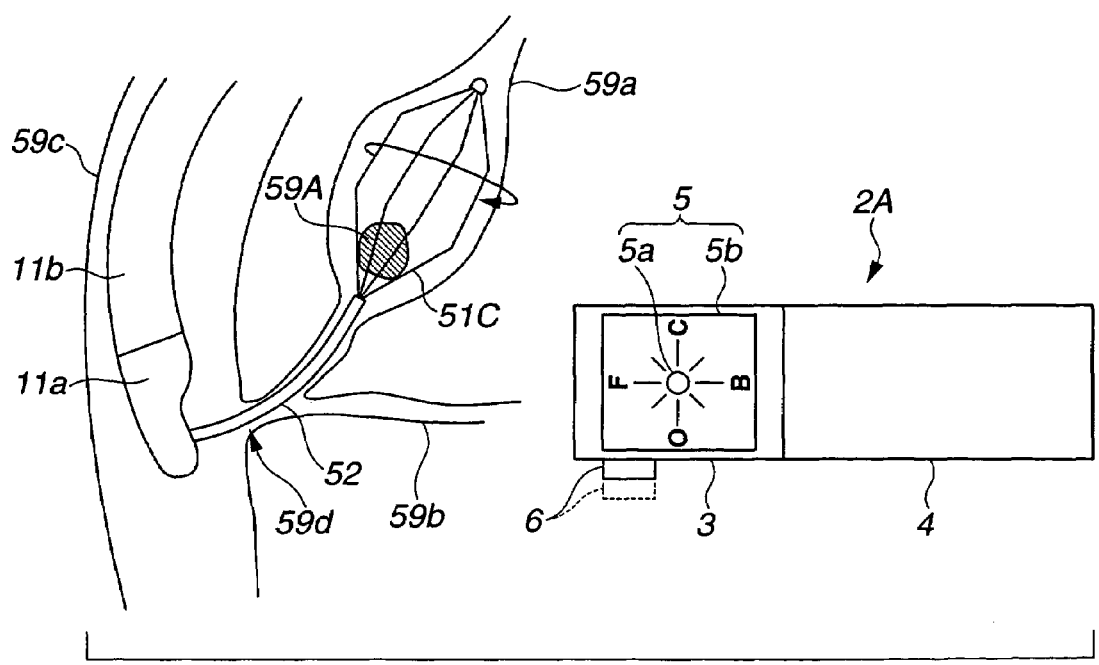
FIG. 21B is a diagram describing a state in which a calculus is taken in a stone extracting basket in a programmed-control state by the basket-forceps program illustrated in FIG. 22.

As shown in step S21 in FIG. 19, the CPU 21 moves the sheath 52 in the arrow d direction, and also performs control for moving the snare portion 51A in the arrow e direction which is linked with movement of the sheath 52. Specifically, the CPU 21 outputs a control signal for advancing the sheath 52 in the arrow d direction a predetermined distance at a predetermined speed which are set on the program beforehand to the electrically-driven advance/retreat device 40 from the second output unit 24b, and also outputs a control signal for retreating the snare portion 51A in the arrow e direction the same distance at the same speed to the electrically-driven operation device 30 from the first output unit 24a.

Subsequently, the CPU 21 determines whether or not movement of the sheath 52 is linked with movement of the snare portion 51A such as shown in step S22. Specifically, the CPU 21 calculates the detection values to be output from the encoders 36c and 44a provided in the respective motors 36 and 44 at the computing processing unit 21b, and determines calculation results thereof at the determining unit 21c.

In the event of determining in step S22 that movement of the sheath 52 is not linked with movement of the snare portion 51A, the CPU 21 proceeds to step S23. In step S23, the CPU 21 performs control for linking movement of the sheath 52 with movement of the snare portion 51A. That is to say, the CPU 21 outputs a control signal for slowing down movement speed or stopping for a predetermined period of time to the device side including the motor at preceding movement side based on the results determined at the determining unit 21c, and then proceeds to step S21.

Figure 18B:
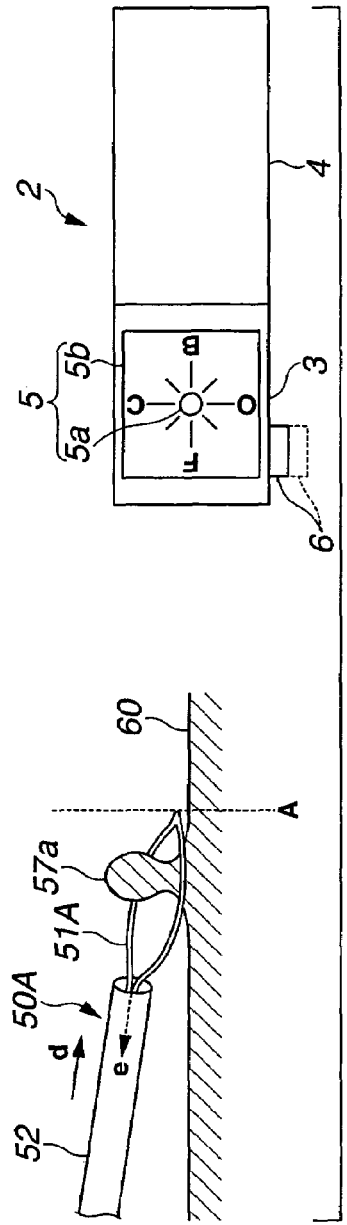
FIG. 18B is a diagram describing a state in which a high-frequency snare is operated in a programmed-control state.

On the other hand, in the event of determining in step S22 that movement of the sheath 52 is linked with movement of the snare portion 51A, the CPU 21 proceeds to step S24. In step S24, the CPU 21 determines whether or not the sheath 52 and the snare portion 51 have moved no less than a predetermined distance based on the detection values to be output from the above encoders 36c and 44a. Thus, the affected portion 57a is not departed from the loop-shaped snare portion 51A, and the loop-shaped snare portion 51A is stored within the sheath 52. That is to say, the loop shape is gradually reduced, which is gradually changed into a state in which the root portion of the affected portion 57a is fastened. In other words, as illustrated in FIG. 18B, in a state in which the position of the tip of the snare portion 51A is held at the position of the dashed line A, an operation for reducing the loop shape without the affected portion 57a being departed from the snare portion 51A is performed.

Figure 18C:
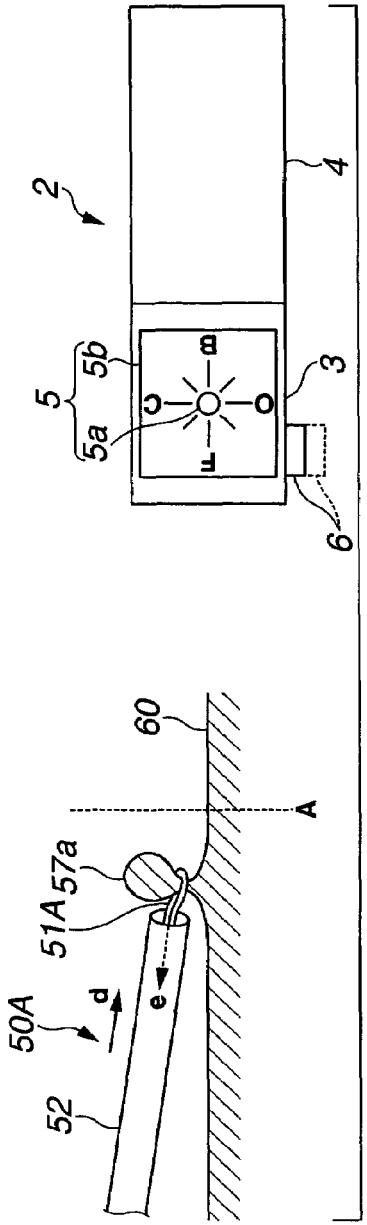
FIG. 18C is a diagram describing a state in which operation of a high-frequency snare is completed in a programmed-control state.

Subsequently, when determining in step S24 that the sheath 52 and the snare portion 51A have moved a predetermined distance in a linked manner, the CPU 21 ends the programmed control. Here, the surgeon may cancel the programmed-control state by turning off the programmed instruction unit 6. At this time, as illustrated in FIG. 18C, the loop shape of the snare portion 51A is reduced, and the root portion of the affected portion 57a is in a state of being fastened. Subsequently, the operating lever 5a returns to a state having a function as the operating lever 5a.

Here, the surgeon observes an endoscope image displayed on the screen of the display device, and visually confirms the fastened state of the affected portion 57a by the snare portion 51A. When determining that the fastened state has no problem, the surgeon operates the foot switch 71 to supply a high-frequency current to the snare portion 51A, and also performs the surgeon's side operation for fastening the affected portion 57a by the snare portion 51A. Thus, the affected portion 57a is excised from the tissue 60.

Note that with the present embodiment, an arrangement is made wherein following the surgeon pushing and operating the programmed instruction unit 6, the programmed control ends by the sheath 52 and the snare portion 51A moving a predetermined distance in a linked manner. However, an arrangement may be made wherein when the surgeon performs an operation for switching an ON state to an OFF state by operating the programmed instruction unit 6 again, the programmed control ends. With this arrangement, when the surgeon instructs a programmed-control state by pushing in and operating the programmed instruction unit 6 provided in the operation instructing device 2, the operating lever 5a has a function as the operating lever 5a. Thus, the surgeon operates the programmed operation instructing unit, and the snare portion is controlled and operated by the high-frequency snare program, whereby even a physician who is inexperienced in treatment can reduce the loop shape to fasten the root of an affected portion without the snare portion being departed from the affected portion, as with a physician who is experienced in treatment.

Also, the high-frequency snare program determines the detection values to be output from the encoders provided in the respective motors, and determines whether or not the sheath and the snare portion are moved in a liked manner. Accordingly, the affected portion is not departed from the snare portion, and a fastened state can be obtained in a sure manner.

Further, with the present embodiment, an arrangement may be made wherein a sensor is provided at the sheath tip portion or the like, thereby determining a fastened state, fastening strength, and so forth.

Also, an arrangement may be made wherein following operating the programmed instruction unit 6 to change to a programmed-control state, the sheath and the snare portion are moved in the opposite direction at a predetermined speed only during the operating lever 5a being leaned and operated. Next, a programmed control example, for example, at the time of collecting a calculus using a basket forceps will be described with reference to FIG. 20 through FIG. 24.

With the endoscope system 1B illustrated in FIG. 20, a treatment tool is a basket forceps 50C, and includes an operation instructing device 2A, and an electrically-driven operation device 30A.

The electrically-driven operation device 30A includes a rotational movement motor 39 for rotationally moving the handle portion 53 of the basket forceps 50C around the long axis of the sheath 55. The rotational movement motor 39 and the control device 20 are electrically connected by a signal cable 39d.

The rotational movement motor 39 is provided with an encoder 39c, and the detection value to be output from the encoder 39c is arranged so as to be output to a third motor obtaining unit 23k via the signal cable 39d.

The motor shaft 39a of the rotational movement motor 39 is provided with a rotational propagating gear (hereinafter, referred to as gear) 39b serving as a spur gear. The rotational movement motor 39 is securely installed at the rear face side of a base body 31a.

The base body 31a includes a hole portion 31c from which the gear 39b of the rotational movement motor 39 is exposed. The base body 31a includes a rotational movement holder (hereinafter, referred to as holder) 31b for rotationally moving and holding the tip portion of the handle portion 53 instead of the installation portion 38. The tip portion of the handle portion 53 of the basket forceps 50C is provided with a driven gear 53a which meshes with the gear 39b.

When the handle portion 53 of the basket forceps 50C is set to the electrically-driven operation device 30A, the information of the IC chip 56 provided in the handle portion 53 is read by the reader/writer 32c, and is output to the treatment-tool information obtaining unit 23c of the signal input unit 23. With the basket forceps 50C also, as with the above embodiment, the slider 55 making up the handle portion 53 is advanced/retreated along the axis of the handle portion 53. With the basket forceps 50C, a stone extracting basket (hereinafter, abbreviated as basket) 51C serving as a function unit is changed to an expanded open state or a stone extracting state along with advance/retreat of the slider 55. An expanded open state is, for example, a state at the time of taking a calculus into the basket, and a stone extracting state is a state in which a calculus has been taken into the basket.

The operation instructing device 2A is provided with a rotational movement instructing unit 5c at the side face which is the positional relation of the opposite side as to the manually-driven operation unit 5 provided in the main body portion 3. The programmed instruction unit 6 is provided, for example, at the right side as viewed from the upper direction toward the tip, for example, at the side face shifted 90 degrees as to the circumferential direction. Now, the operation instructing device 2A includes, for example, a recessed portion 5d, which is arranged so as to be disposed in a flexible tube portion 11c. Accordingly, the programmed instruction unit 6 or the like can be operated while gripping the flexible tube portion 11c.

The rotational movement instructing unit 5c is a switch for selecting regarding whether to drive the rotational movement motor 39. The rotational movement instructing unit 5c is in an OFF state when being orthogonal to the longitudinal axis of the operation instructing device 2A. The rotational movement instructing unit 5c can be leaned and operated in the tip-wards direction and in the base direction from the initial position which is an OFF state. Upon the rotational movement instructing unit 5c being leaned and operated, a rotational movement instructing signal is output to the manually-driven signal processing unit 23a via the signal cable 2a extending from the grip body 4. Specifically, in a manually-driven operating state, upon the rotational movement instructing unit 5c being leaned in the tip-wards direction, the basket 51C rotates counterclockwise toward the tip from the base. On the other hand, upon the rotational movement instructing unit 5c being leaned toward the base side, the rotational movement instructing unit 5c rotates clockwise toward the tip from the base.

That is to say, as described in the above embodiment, the surgeon can change the basket 51C to an expanded open state and a stone extracting state by operating the operating lever 5a with the thumb or the like. In addition, the surgeon can rotationally move and operate the basket 51C around the axis by operating the rotational movement instructing unit 5c with the index finger or the like.

With the present embodiment also, rotating speed is arranged so as to be changed by changing the leaning angle of the rotational movement instructing unit 5c. That is to say, as the leaning angle of the rotational movement instructing unit 5c is increased as to the initial position, rotating speed gradually becomes faster.

Note that the endoscope to be used at the time of inserting the basket forceps 50C into the bile duct 59a or the like is a lateral-vision-type endoscope. With the present embodiment, description will be made regarding the respective components of a lateral-vision-type endoscope using the same reference symbols as the respective components of the above endoscope 10 for the sake of facilitating description thereof. Also, with the operation instructing device 2A to be used for the present embodiment, the operating lever supporting portion 5b is arranged to be printed with a reference mark "F" indicating advance toward the tip side, a reference mark "B" indicating retreat toward the base side, a reference mark "O" indicating an expanded open state at the lower side in the drawing which is the left side, and a reference mark "C" indicating a stone extracting state at the upper side in the drawing which is the right side.

With the endoscope system 1B wherein the handle portion 53 of the basket forceps 50C is disposed in the electrically-driven operation device 30A, a basket-forceps program is activated by the surgeon pushing in and operating the programmed instruction unit 6 provided in the operating instruction device 2A. In a programmed-control state, the operating lever 5a according to the present embodiment loses a function as the operating lever 5a, and also a function as a selection switch.

The surgeon disposes the tip portion 11a of the lateral-vision-type endoscope 10 in the vicinity of the papillary area 59d of the duodenum 59c while observing an endoscope image. Subsequently, the surgeon installs and disposes the sheath 52 of the basket forceps 50C into the bile duct 59a while observing an endoscope image. Subsequently, following the basket 51c being guided out from the inside of the sheath 52 in an operating state at the surgeon's side, the surgeon changes the basket 51C into an expanded open state of being extended within the bile duct 59a, such as illustrated with the arrow in FIG. 21A. Here, in the event of desiring an operation by programmed control, the surgeon pushes in and operates the programmed instruction unit 6 provided in the operation instructing device 2. Thus, the CPU 21 selects and executes the basket-forceps program registered on the storage device 22, as shown in steps S5 through S7 in FIG. 10, to enter a programmed-control state.

Figure 22:
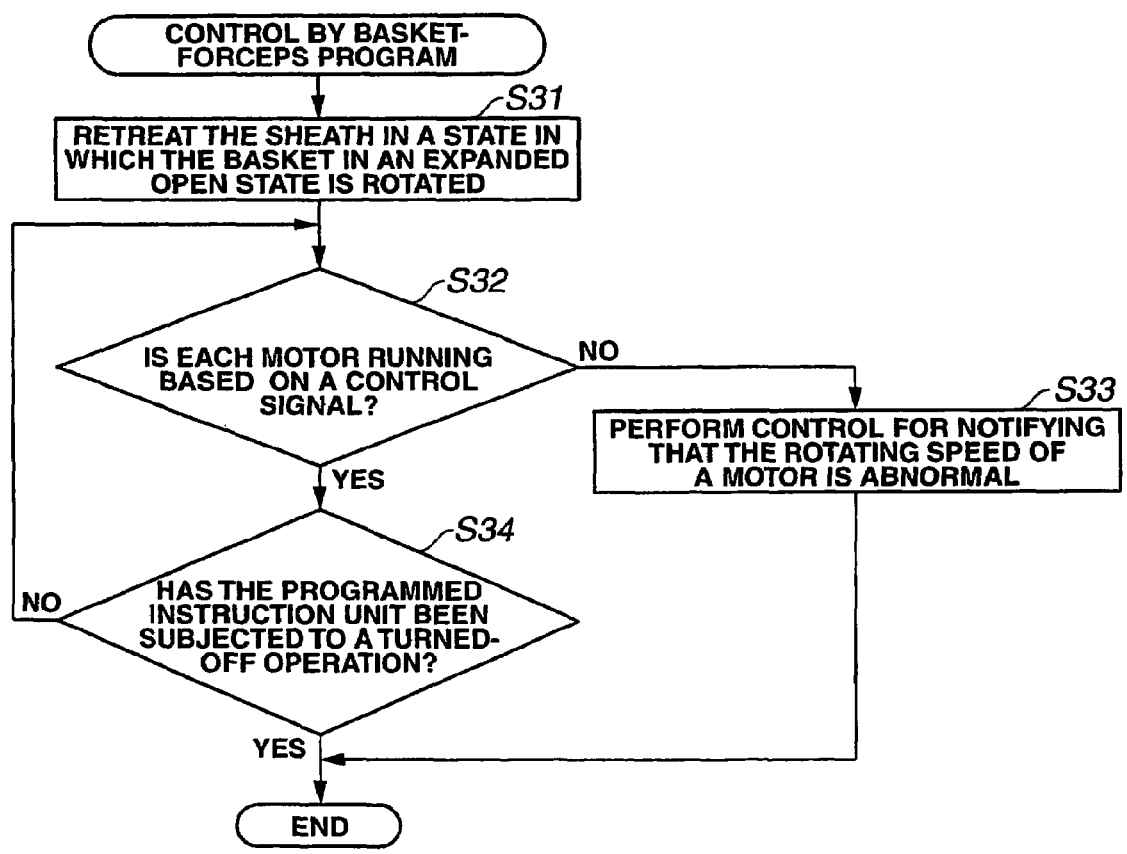
FIG. 22 is a diagram describing one control example using a basket-forceps program.

As shown in step S31 in FIG. 22, in order for the CPU 21 to take the calculus 59A into the basket 51C, the CPU 21 outputs two control signals to the electrically-driven operation device 30 from the first output unit 24a simultaneously, and on the other hand, outputs a control signal for retreating the sheath 52 to the electrically-driven advance/retreat device 40 from the second output unit 24b. Then, the basket 51C is kept in an expanded open state, rotates in a predetermined direction, for example, clockwise, and also the sheath 52 retreats at a predetermined constant speed.

In step S32, the CPU 21 confirms an operating state. That is to say, in order to determine whether or not the motors 36, 39, and 44 operate based on a control signal, the CPU 21 subjects the detection values to be input to the motor obtaining units 23h, 23j, and 23k to computing processing at the computing processing unit 21b, and then determines the difference between the actual rotating state and the number of rotations instructed by a control signal at the determining unit 21c.

In the event of confirming in step S32 that the respective motors 36, 39, and 44 operate based on a control signal, the CPU 21 proceeds to step S34. In step S34, the CPU 21 proceeds to step S31 to retreat the basket 51C in a rotating state until the programmed instruction unit 6 being turned off.

On the other hand, in the event of detecting an abnormal rotation of any one of the motors 36, 39, and 44, the CPU 21 proceeds to step S33. In step S34, the CPU 21 outputs a control signal for informing abnormality to inform the surgeon that the number of rotations of the motor is abnormal, and ends programmed control.

When ending programmed control, the surgeon turns off the programmed instruction unit 6 as shown in step S34. Thus, the CPU 21 ends programmed control.

Note that in step S32 the respective motors 36, 39, and 44 are operated based on a control signal, whereby the calculus 59A is stored in the basket 51C, and the calculus 59A stored in the basket 51C is taken out of the bile duct 59a. At this time, the surgeon confirms from the endoscope image displayed on the screen of the display device that the calculus 59A is sampled, following which turns off the programmed instruction unit 6.

Thus, the surgeon operates the programmed operation instructing unit, and the basket is controlled and operated by the basket-forceps program, whereby even a physician who is inexperienced in treatment can perform sampling of a calculus or the like, in a sure manner, in a short period of time by retreating the sheath while rotating the basket, as with a physician who is experienced in treatment.

Figure 23A:
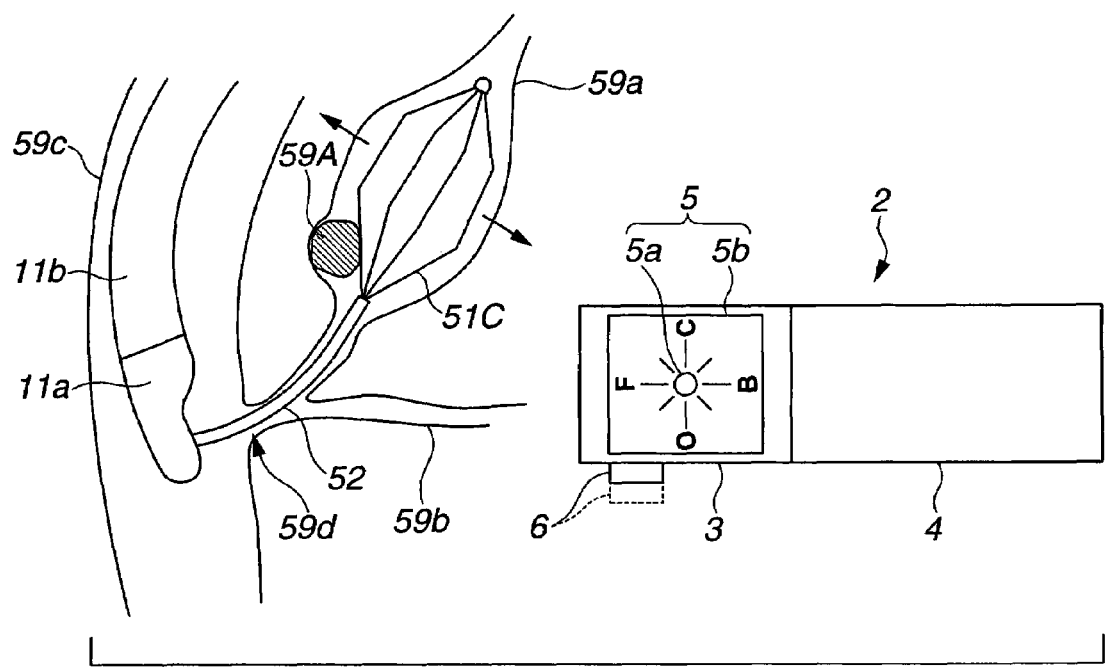
FIG. 23A is a diagram describing a state when determination is made regarding whether to operate a basket forceps manually or by programmed control.
Figure 23B:
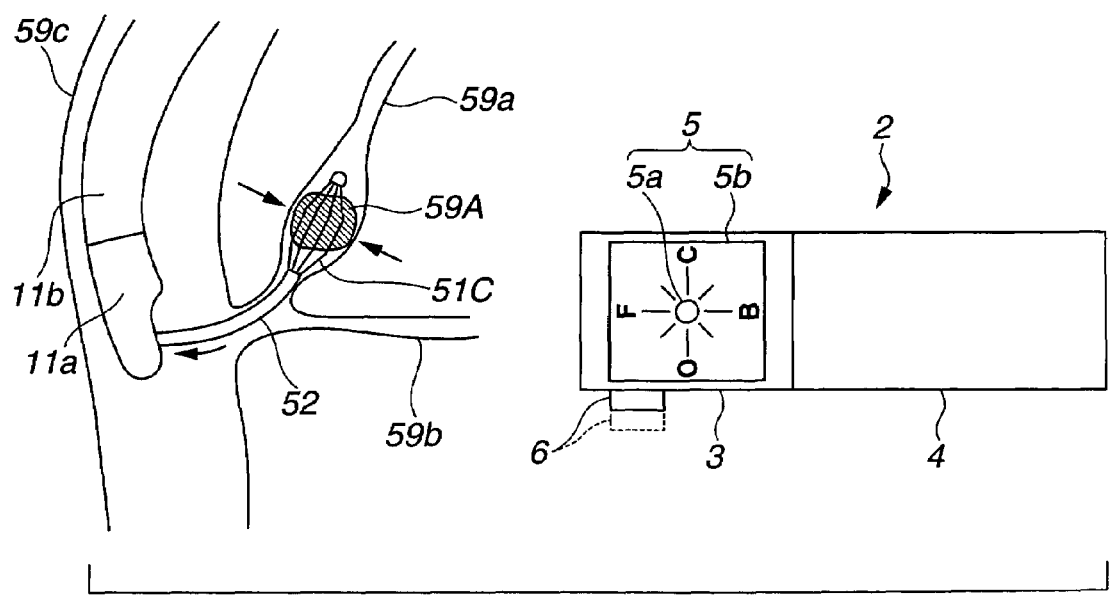
FIG. 23B is a diagram describing a state in which a calculus is taken in a stone extracting basket in a programmed-control state by the basket-forceps program illustrated in FIG. 24.

Now, a control example using another basket-forceps program will be described with reference to FIG. 23A, FIG. 23B, and FIG. 24.

As described above, the surgeon installs and disposes the sheath 52 of the basket forceps 50C into the bile duct 59a while observing an endoscope image. Subsequently, the surgeon guides the basket 51C out from the sheath 52 in an operating state at the surgeon's side, following which changes the basket 51C into an expanded open state of being extended within the bile duct 59a such as illustrated with the arrow in FIG. 26A. Here, in the event of desiring an operation by programmed control, the surgeon pushes in and operates the programmed instruction unit 6 provided in the operation instructing device 2. Thus, the CPU 21 enters a programmed-control state by the basket-forceps program.

Figure 24:
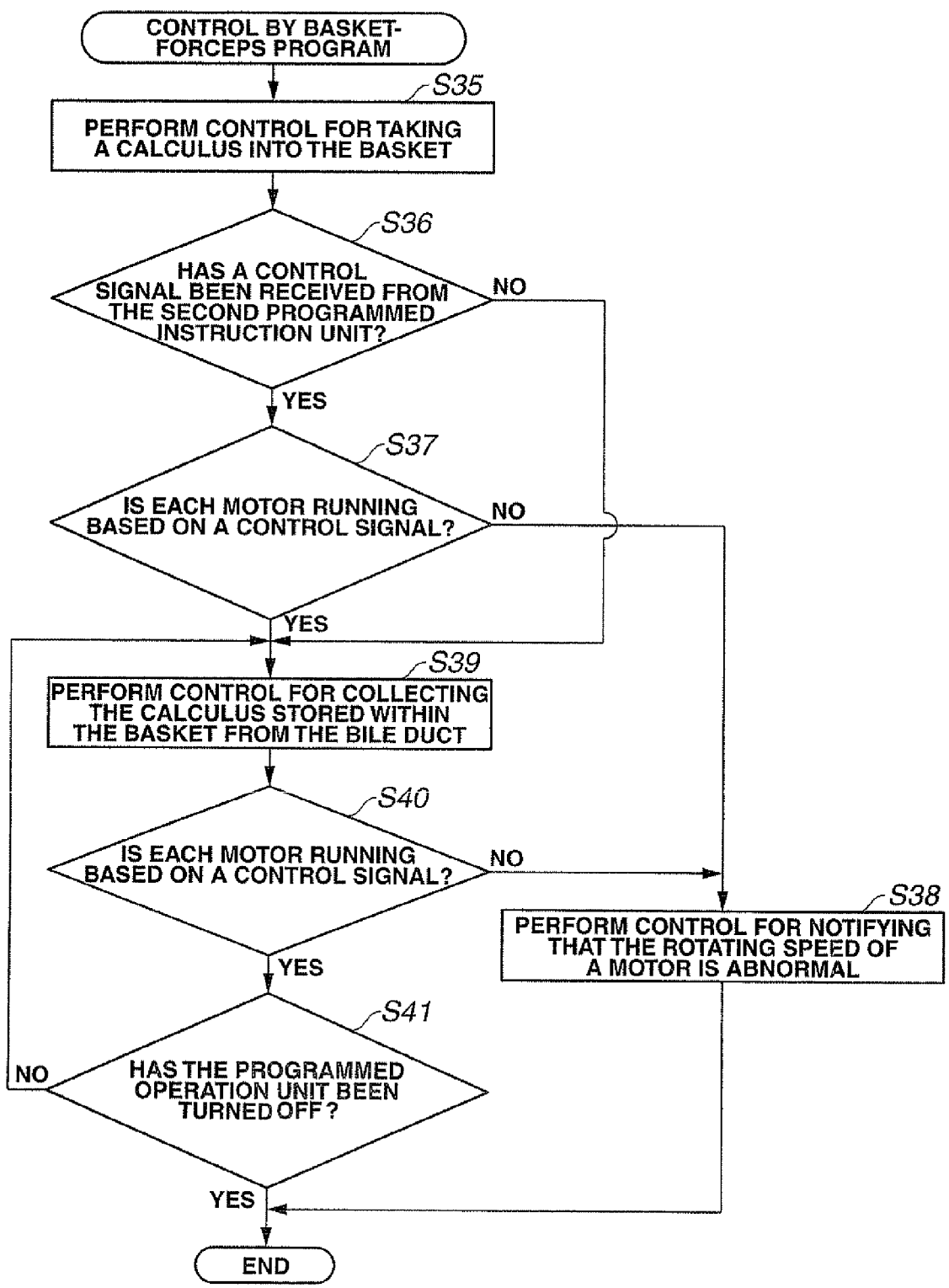
FIG. 24 is a diagram describing another control example by a basket-forceps program.

As shown in step S35 in FIG. 24, the CPU 21 performs control for taking the calculus 59A into the basket 51C. Specifically, the CPU 21 outputs two control signals to the electrically-driven operation device 30 from the first output unit 24a simultaneously, i.e., outputs a control signal for rotating the basket 51C in a predetermined direction, e.g., clockwise, and a control signal for retreating the slider 55 so as to change the interval of wires making up the basket 51C into an expanded state and a narrowed state at a predetermined time interval. During this operation, the position of the sheath 52 is kept at the initial position.

Thus, the position and orientation at which the wires making up the basket 51C come into contact are changed as to the calculus 59A, and storing of the calculus 59A into the basket 51C is performed.

In an operating state in step S35, the CPU 21 performs processing for determining whether or not the motors 36, 39, and 44 are operated based on a control signal shown in step S36, and processing for confirming output of a control signal from the second programmed instruction unit shown in in step S37. In step S36, the CPU 21 subjects the detection value to be input to the motor obtaining units 23h, 23j, and 23k to computing processing at the computing processing unit 21b, following which determines the difference between the actual rotating state and the number of rotations instructed by a control signal at the determining unit 21c.

In the event of detecting an abnormal rotation of any one of the motors 36, 39, and 44 in step S36, the CPU 21 proceeds to step S38. Here, the CPU 21 outputs a control signal for informing abnormality to inform the surgeon that there is abnormality in rotations of the motor, and ends programmed control. On the other hand, in the event of confirming operations based on a control signal in step S36, the CPU 21 proceeds to step S37.

The surgeon confirms on an X-ray image regarding whether or not the calculus 59A is stored in the basket 51C. Subsequently, upon confirming that the calculus 59A being stored in the basket 51C, the surgeon operates, for example, the second programmed instruction unit (not shown) to perform control for collecting the calculus 59A stored in the basket 51 from the bile duct. Then, the CPU 21 confirms output of a control signal from the second programmed instruction unit in step S37, and proceeds to step S39.

The CPU 21 starts control for collecting the calculus 59A stored in the basket 51C in step S39. That is to say, the CPU 21 outputs a control signal for rotating the basket 51C to the electrically-driven operation device 30 from the first output unit 24a, and a control signal for retreating the sheath 52 to the electrically-driven advance/retreat device 40 from the second output unit 24b. Thus, the basket 51C rotates at a predetermined constant speed, and also in this state, the sheath 52 retreats at a predetermined constant speed.

In an operating state in step S39, the CPU 21 performs processing for determining whether or not the motors 39 and 44 are rotated based on a control signal such as shown in step S40. That is to say, the CPU 21 subjects the detection value to be input to the motor obtaining units 23j and 23k to computing processing at the computing processing unit 21b, following which determines the difference between the actual rotating state and the number of rotations instructed by a control signal at the determining unit 21c.

In the event of detecting an abnormal rotation of either of the motors 39 and 44 in step S40, the CPU 21 proceeds to step S38. Here, the CPU 21 outputs a control signal for informing abnormality in the number of rotations to inform the surgeon that there is abnormality in rotations of the motor, and ends programmed control.

In the event of confirming operations based on a control signal in step S40, the CPU 21 proceeds to step S41. As shown in step S41, the programmed instruction unit 6 is turned off, thereby ending programmed control.

Note that in step S40 the respective motors 39 and 44 are operated based on a control signal, whereby the basket 51C storing the calculus 59A is taken out from the bile duct 59a. At this time, the surgeon confirms from the endoscope image displayed on the screen of the display device that the calculus 59A is sampled, following which turns off the programmed instruction unit 6.

Thus, even a physician who is inexperienced in treatment can perform sampling of a calculus by rotating the basket, a stone extracting operation, and an operation for retreating the sheath, as with a physician who is experienced in treatment.

Now, with the present embodiment also, an arrangement may be made wherein a sensor is provided, thereby determining whether or not the calculus has been contained in the basket.

An injector program control example such as injecting a drug solution using an injector will be described with reference to FIG. 25 through FIG. 27.

With the endoscope system 1C illustrated in FIG. 25, a treatment tool is an injection needle 80, and includes an injector 50D and an electrically-driven operation device 30B.

The injection needle 80 includes a sheath 83 which is a guide tube integral with a fixing unit 82 making up a handle portion. A needle tube 81 is disposed within the sheath 83, which can advance and retreat. The base portion of the needle tube 81 is securely installed on a slider portion 84 which is slidable as to the fixing unit 82. The needle tip of the needle tube 81 is a function unit, and a sensor (not shown) for detecting that this needle tip is inserted into tissue by change in a resistance value is provided at the needle tip. The detection value of this sensor is arranged so as to be output to the first sensor obtaining unit 23f.

The base portion of the slider portion 84 making up the injection needle 80 is arranged so as to be connected with the injector 50D via a tube 52. The injector 50D is for injecting a drug solution, physiological saline, or the like into tissue, and for example, physiological saline is pooled in internal space made up of an outer cylinder 53c and an inner cylinder 53b.

In order to operate the injector 50D, with the electrically-driven operation device 30B, a part of the specification differs from the above electrically-driven operation device 30. Specifically, the electrically-driven operation device 30B includes a fixing unit 31d instead of the installation portion 38 at the base body 31, and eliminates the use of the ring-retainer portion 32. The fixing unit 31d is disposed with the outer cylinder 53c of the injector 50D. Also, the rack 35 is attached with an inner cylinder holder 33b instead of the slider-retainer portion 33 including the holder 33a. The inner cylinder holder 33b holds the end portion of the inner cylinder 53b of the injector 50D. Note that with the present embodiment, the reader/writer 32c is provided in the fixing unit 31d.

Upon the outer cylinder 53c of the injector 50D being set to the electrically-driven operation device 30B, the information of the IC chip 56 provided in the outer cylinder 53c is read by the reader/writer 32c, and is output to the treatment-tool information obtaining unit 23c of the signal input unit 23. With the injector 50D, as with the above embodiment, the inner cylinder 53b inserted into the outer cylinder 53c is advanced or retreated along the axis of the injector 50D. With the injector 50D, the pooled physiological saline is poured out from the needle tip of the needle tube 81 to the outside along with advancement of the inner cylinder 53b.

With the endoscope system 1C wherein the outer cylinder 53c of the injector 50D is disposed in the electrically-driven operation device 30B, an injector program is activated by the surgeon pushing in and operating the programmed instruction unit 6 provided in the operation instructing device 2. In a programmed-control state, the operating lever 5a according to the present embodiment loses a function as the operating lever 5a, and a function as a selection switch.

Figure 26A:
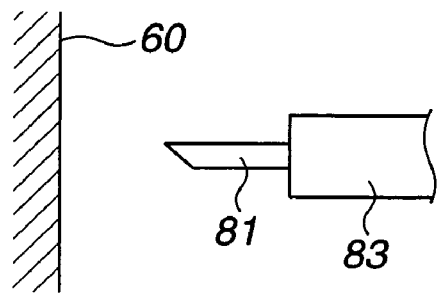
FIG. 26A is a diagram describing a state when determination is made regarding whether to inject liquid manually or by programmed control.

The surgeon inserts the insertion unit 11 of the endoscope 10 toward a target portion within the body cavity while observing an endoscope image. Subsequently, the surgeon confronts the tip portion 11a of the insertion unit 11 with the tissue 60 while observing an endoscope image on the screen. Subsequently, the surgeon disposes the sheath 83 in the vicinity of the tissue 60 in an operating state at the surgeon's side in a state wherein the needle tube 81 is protruded such as illustrated in FIG. 26A while observing an endoscope image. Here, in the event of desiring an operation by programmed control, the surgeon pushes in and operates the programmed instruction unit 6 provided in the operation instructing device 2. Thus, the CPU 21 selects and executes the injector program registered on the storage device 22 such as shown in steps S5 through S7 in FIG. 10 to be in a programmed-control state.

Figure 27:
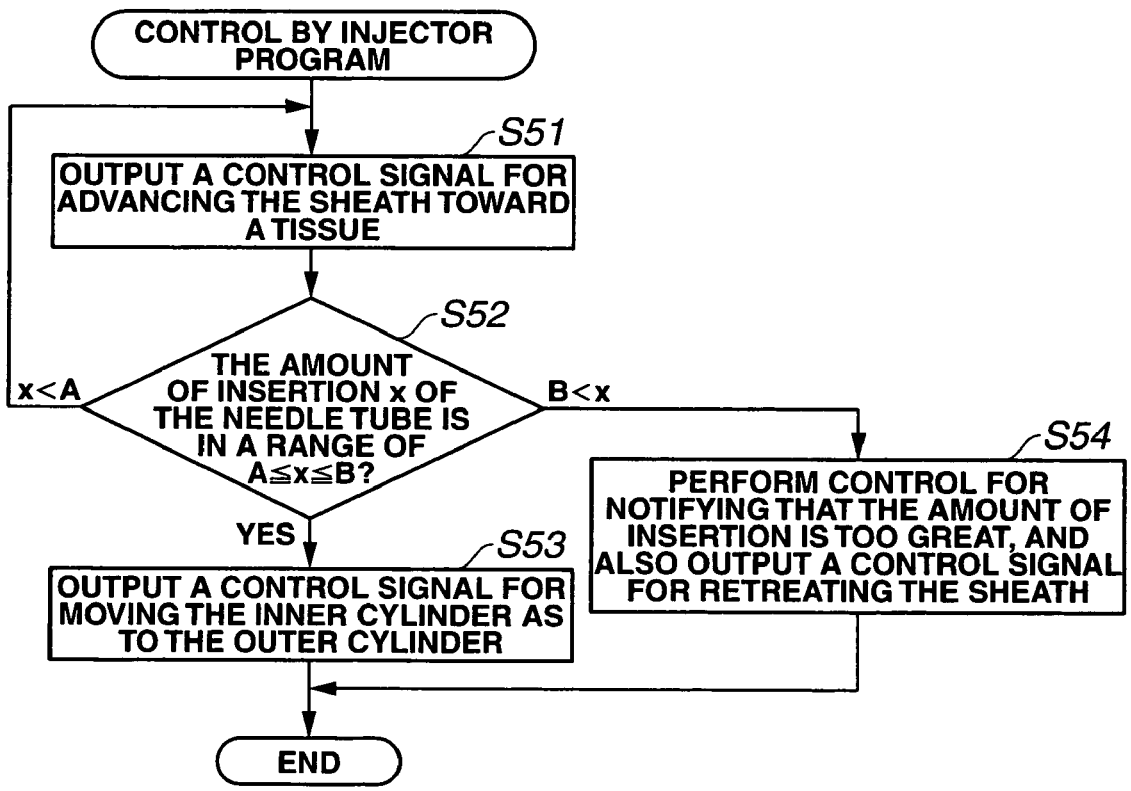
FIG. 27 is a diagram describing one control example using an injector program.

As shown in step S51 in FIG. 27, the CPU 21 performs control for advancing the sheath 83 toward the tissue 60. That is to say, the CPU 21 outputs a control signal for advancing the needle tube 81 at a predetermined speed toward the tissue 60 to the electrically-driven advance/retreat device 40 from the second output unit 24b. The CPU 21 outputs the control signal for instructing advancement, following which proceeds to step S52, calculates the amount of insertion X at the computing processing unit 21b from an electrical signal to be output from a sensor provided at the tip of the needle tube 81 to the first sensor obtaining unit 23f, and determines at the determining unit 21c whether or not the calculated amount of insertion X is appropriate.

That is to say, in step S52 the CPU 21 determines whether or not the amount of insertion X calculated from a current signal output from the sensor is in a range of $A \leq X \leq B$.

Here, when determining that the amount of insertion X is in a range of $A \leq X \leq B$, the CPU 21 proceeds to step S53. In step S53, the CPU 21 performs control for injecting the physiological saline pooled in the injector 50D into tissue only for a predetermined amount. That is to say, the CPU 21 outputs a control signal for moving the inner cylinder 53b a predetermined distance as to the outer cylinder 53c to the electrically-driven operation device 30B from the first output unit 24a.

Subsequently, the CPU 21 confirms the amount of movement of the inner cylinder 53c from the amount of rotations of the motor 36, and when determining that the inner cylinder 53c has moved a predetermined distance, the CPU 21 ends programmed control. Thus, the function of the operating lever 5a is in an operable state.

Figure 26B:
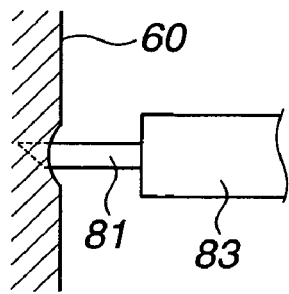
FIG. 26B is a diagram describing a state in which a needle tube punctures tissue in a programmed-control state.
Figure 26C:
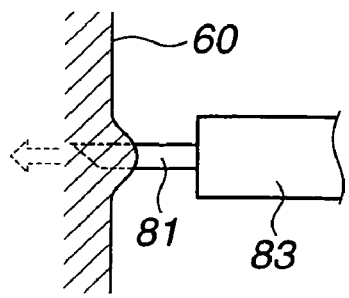
FIG. 26C is a diagram describing a state in which the liquid of an injector is injected through the needle tube in a programmed-control state.

Here, the surgeon confirms the protruding state of the tissue 60 which the physiological saline is injected into and is protruded as illustrated in the dashed-line arrow such as illustrated in FIG. 26C. That is to say, the surgeon determines from an endoscope image displayed on the screen of the display device whether or not the injection state of the physiological saline into the tissue 60 is a desired state.

When determining that the injection state is sufficient, the surgeon operates the operating lever 5a to remove the needle tube 81 from the tissue 60. On the other hand, when determining that the injection state is insufficient, the surgeon operates the operating lever 5a to further inject physiological saline into the tissue, following which removes the needle tube 81 from the tissue 60.

On the other hand, in the event that in step S52 the CPU 21 determines that the amount of insertion X is less than A, i.e., $X<A$, the CPU 21 proceeds to step S51. Also, in the event that in step S52 the CPU 21 determines that the amount of insertion X is greater than B, i.e., $B<X$, the CPU 21 proceeds to step S54, performs control for informing that the amount of insertion is too large, and also outputs a control signal for retreating the sheath 83. Thus, the surgeon confirms retreating of the sheath 83, following which ends programmed control. Here, in the event of performing reinsertion, the surgeon turns on the programmed instruction unit 6.

As described above, the surgeon operates the programmed operation instructing unit, and injection of physiological saline or the like into tissue is selected by the injector program, whereby even a physician who is inexperienced in treatment can insert the needle tube into tissue for a predetermined amount to inject physiological saline or the like, as with a physician who is experienced in treatment. Thus, a problem such as insufficient protrusion caused by the needle tube being inserted insufficiently, and on the contrary, inserting the needle tube deeper than a target portion can be prevented in a sure manner.

Also, according to the injector program, the amount of insertion of the needle tube to be inserted into tissue is determined based on the electric signal to be output from the sensor. Accordingly, injection can be performed in a sure manner only when the amount of insertion X of the needle tube is in a range of $A \leq X \leq B$.

Further, according to the injector program, determination is made whether or not reinjection is performed by confirming the insertion state in the vicinity of the needle tube following injection into tissue, whereby it can be selected whether or not reinjection is necessary, and accordingly, even a physician who is inexperienced in treatment can inject the most appropriate amount of physiological saline or the like into tissue, as with a physician who is experienced in treatment.

Note that with the present embodiment, an arrangement is made wherein following physiological saline being injected into tissue for a predetermined amount, programmed control is terminated. However, an arrangement may be made wherein operation by programmed control is immediately terminated by a surgeon turning off the programmed instruction unit 6.

Also, with the present embodiment, an arrangement is made wherein under control of the CPU 21, following advance control shown in step S51, determination of the amount of insertion X shown in step S52, and injection of, for example, physiological saline into tissue shown in step S53, programmed control is terminated. However, as shown in the following, an arrangement may be made wherein programmed control is performed.

As described above, the surgeon confronts the tip portion 11a of the insertion unit 11 with the tissue 60 while confirming an endoscope image on the screen. Subsequently, the surgeon inserts the needle tube 81 into the tissue 60a little as illustrated in FIG. 26B in an operating state at the surgeon's side while observing an endoscope image. Here, in the event of desiring an operation by programmed control, the surgeon pushes in and operates the programmed instruction unit 6. Then, the CPU 21 selects and executes the injector program to be in a programmed-control state. In this programmed-control state, the operating lever 5a according to the present embodiment serves as a selection switch. Specifically, the operating lever 5a is leaned and operated to, for example, the reference mark B side, thereby outputting an instructing signal for stopping advancement of the sheath 83, and the operating lever 5a is leaned and operated to, for example, the reference mark C side, thereby outputting an instructing signal for stopping injection of physiological saline.

Figure 28:
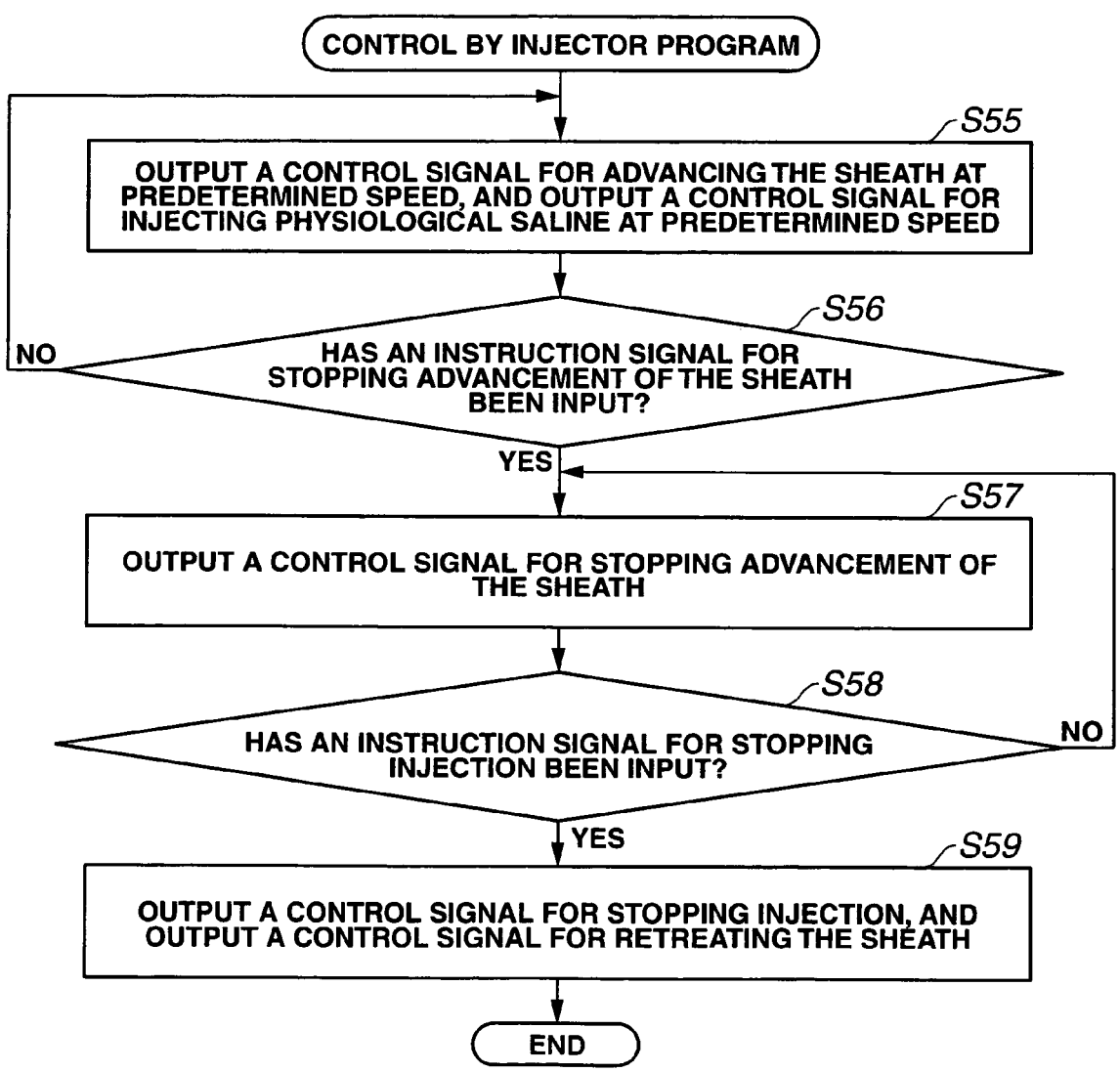
FIG. 28 is a diagram describing another control example using an injector program.

As shown in step S55 in FIG. 28, the CPU 21 performs control for advancing the sheath 83 at a predetermined speed, and control for advancing the inner cylinder 53b. Thus, the needle tube 81 is inserted into the tissue 60 at a predetermined speed. The surgeon confirms this situation by an endoscope image displayed on the screen.

The CPU 21 performs control for advancing the sheath 83 and control for advancing the inner cylinder 53b, following which proceeds to step S56, and confirms whether or not there is an instructing signal for stopping advancement of the sheath 83. That is to say, the CPU 21 monitors whether or not an instructing signal for informing that the operating lever 5a is leaned and operated to the reference mark B side is input to the manually-driven signal processing unit 23a. The sheath 83 continues to advance, and also the inner cylinder 53b continues to advance until the CPU 21 confirms this instructing signal. That is to say, in a state in which physiological saline is injected into the tissue from the needle tube 81, the needle tube 81 is inserted at a predetermined speed.

On the other hand, upon confirming in an endoscope image that the tissue starts to protrude, the surgeon determines that the needle tube 81 has been inserted into a correct position. Subsequently, the surgeon leans and operates the operating lever 5a to the reference mark B side to output an instructing signal for stopping advancement of the sheath 83.

Upon confirming the instructing signal for stopping advancement of the sheath 83 in step S56, the CPU 21 proceeds to step S57 to output a control signal for stopping the sheath 83. Thus, advancement of the sheath 83 is stopped, and only injection of physiological saline is performed.

The CPU 21 outputs the control signal for stopping the sheath 83 in step S57, following which proceeds to step S58 to confirm whether or not there is the instructing signal for stopping advancement of the inner cylinder 53b. That is to say, the CPU 21 monitors whether or not an instructing signal for informing that the operating lever 5a is leaned and operated to the reference mark C side is input to the manually-driven signal processing unit 23a. The inner cylinder 53b continues to advance until the CPU 21 confirms this instructing signal. That is to say, physiological saline is injected into the tissue from the needle tube 81.

The surgeon confirms the protruding state of the tissue 60 from an endoscope image to determine whether or not the injection state of physiological saline is a desired state. Subsequently, when determining that the injection state has reached a desired state, the surgeon leans and operates the operating lever 5a to the reference mark C side. Then, an instructing signal for stopping advancement of the inner cylinder 53b is output from the operating lever 5a.

Upon the CPU 21 confirming the instructing signal for stopping advancement of the inner cylinder 53b in step S58, the CPU 21 proceeds to step S59 to output a control signal for stopping advancement of the inner cylinder 53b, and also output a control signal for retreating the sheath 83. Thus, advancement of the inner cylinder 53b is stopped, injection of physiological saline is stopped, and the needle tube 81 is removed from the tissue 60. The CPU 21 confirms removal of the needle tube 81, following which ends programmed control.

Figure 29:
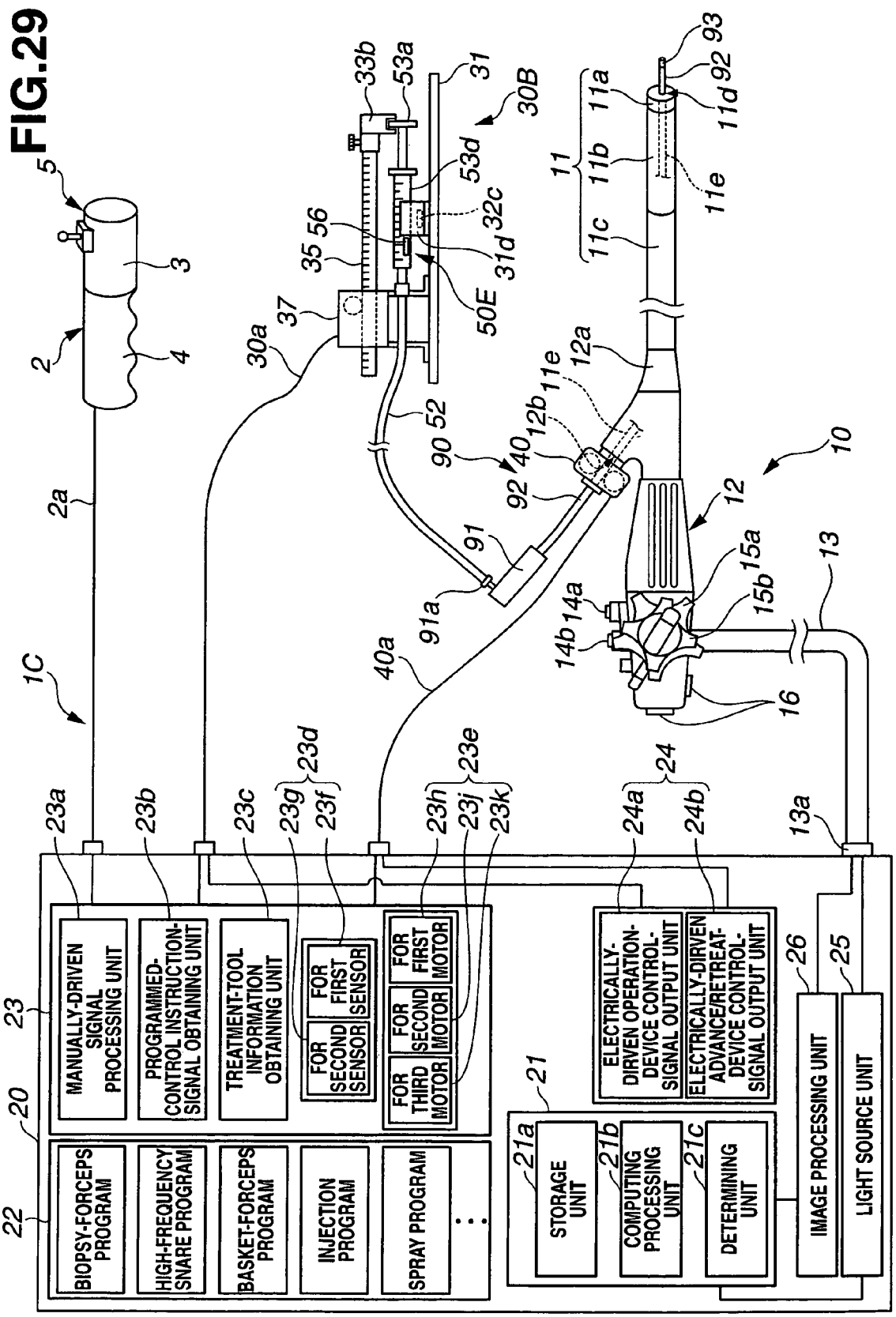
FIG. 29 is a diagram describing the overall configuration of an endoscope system in which a treatment tool is a spray tube.

With the above endoscope system IC, a treatment tool may be a spray tube 90 for spraying the pigment as illustrated in FIG. 29. With this system, a spray device 50E pooling the pigment is attached to the electrically-driven operation device 30B instead of the injector.

With the present embodiment, upon the device main body 53d of the spray device 50E being set to the electrically-driven operation device 30B, the information of the IC chip 56 provided in the device main body 53d is read by the reader/writer 32c, and is output to the treatment-tool information obtaining unit 23c of the signal input unit 23. With the spray device 50E also, as with the above embodiment, a piston 53e which is slidably provided in the device main body 53d is advanced or retreated along the axis of the spray device 50E. With the spray device 50E, an arrangement is made wherein the pigment pooled in the device main body 53d is sprayed from a nozzle portion 93 serving as a function unit provided at the tip portion of the sheath 92 of a spray tube 90 to the outside along with advancement of the piston 53e.

With the present embodiment, the tube 52 of the spray device 50E is detachably attached to a collet portion 91a provided at the side portion of the main body portion 91 of the spray tube 90.

With the endoscope system 1 wherein the device main body 53d of the spray device 50E is disposed in the electrically-driven operation device 30B, a spray program is activated by the surgeon pushing in and operating the programmed instruction unit 6 provided in the operation instructing device 2. In a programmed-control state, the operating lever 5a according to the present embodiment loses a function as the operating lever 5a, and also a function as a selection switch.

The surgeon inserts the insertion unit 11 of the endoscope 10 toward a target portion within a body cavity of a subject while observing an endoscope image. Subsequently, the surgeon confirms an endoscope image on the screen to let the tip portion 11a of the insertion unit 11 reach a desired portion within a lumen. Here, in the event of desiring pigment spray by programmed control, the surgeon pushes in and operates the programmed instruction unit 6 provided in the operation instructing device 2. Thus, the CPU 21 selects and executes the spray program registered on the storage device 22 such as shown in steps S5 through S7 in FIG. 10 to enter a programmed-control state.

Figure 30:
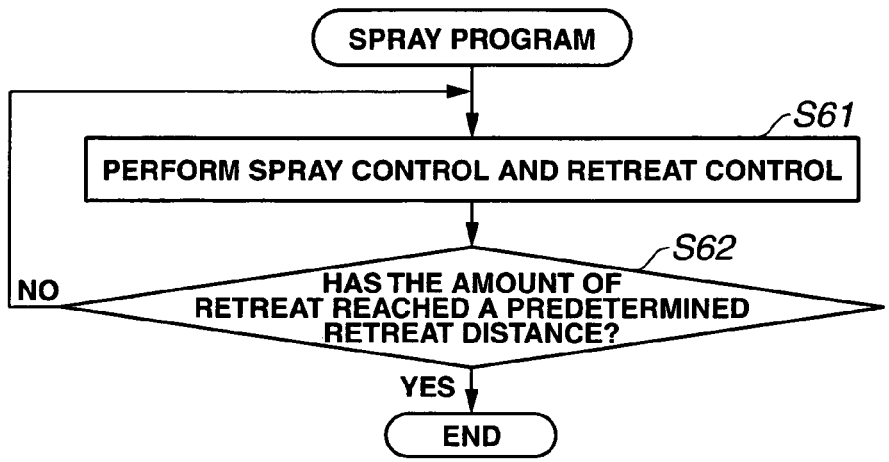
FIG. 30 is a diagram describing a control example using a spray program.

As shown in step S61 in FIG. 30, the CPU 21 starts spraying as to the target portion. That is to say, the CPU 21 outputs a control signal to the electrically-driven operation device 30B from the first output unit 24a, and also outputs a control signal to the electrically-driven advance/retreat device 40.

Figure 31A:
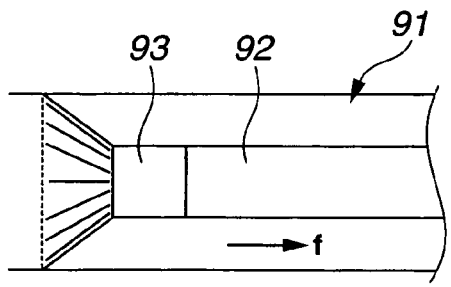
FIG. 31A is diagram describing a state in which the pigment is sprayed in a programmed-control state.

Then, as illustrated in FIG. 31A, the piston 53e of the spray device 50E is moved at a predetermined constant speed, and the pigment is sprayed from the nozzle portion 93 of the spray tube 90, and also the spray tube 90 retreats in the arrow f direction at a predetermined constant speed.

Figure 31B:
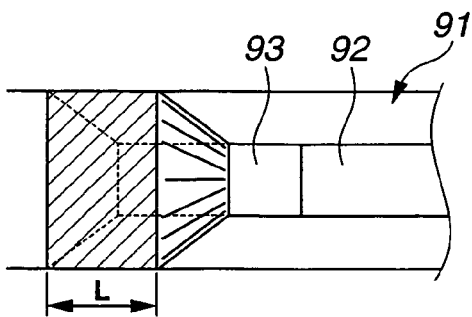
FIG. 31B is a diagram describing a state in which the pigment is sprayed over the entire inner wall in a programmed-control state.

Subsequently, the CPU 21 determines the amount of retreat of the spray tube 90 retreated as shown in step S62. That is to say, the CPU 21 obtains the amount of retreat at the computing processing unit 21b based on the detection value to be output from the encoder 36c provided in the motor 36, and determines at the determining unit 21c whether or not the amount of retreat has reached a predetermined retreat distance (L). In step S52, the CPU 21 continues to perform spray until the amount of retreat reaches the retreat distance L, and when determining that the amount of retreat has reached the retreat distance L, the CPU 21 ends programmed control. At this time, as illustrated in FIG. 31B, the pigment is in a state of being evenly adhered across the entire inner wall of the distance L of the lumen as illustrated in FIG. 31B.

Thus, an arrangement is made wherein the surgeon operates the programmed operation instructing unit, and spray of the pigment is performed as to a live body tissue by the spray program, whereby even a physician who is inexperienced in treatment can evenly spray the pigment pooled in the spray device as to tissue while retreating the sheath, as with a physician who is experienced in treatment.

Also, with the above endoscope system 1A, a treatment tool may be a marking device 50F, as illustrated in FIG. 32.

With this system, the handle portion 53f of the marking device 50F can be attached to the electrically-driven operation device 30.

The marking device 50F comprises an insulation sheath 101, and a needle scalpel 102. Upon the finger-hooking ring 54 of the handle portion 53f being set to the ring-retainer portion 32 of the electrically-driven operation device 30, the information of the IC chip 56 provided in the handle portion 53 is read by the reader/writer 32c, and is output to the treatment-tool information obtaining unit 23c of the signal input unit 23. With the marking device 50F also, as illustrated in FIG. 32, the slider 55 making up the handle portion 53f is advanced or retreated along the axis of the handle portion 53f. With the marking device 50F, upon advancing the slider 55, the needle scalpel 102 serving as a function unit protrudes from the tip of the insulation sheath 101. Upon retreating the slider 55 in such a state, the needle scalpel 102 is stored within the insulation sheath 101.

The slider 55 of the marking device 50F to be used for the present embodiment is provided with a high-frequency wiring cord 70a. The high-frequency wiring cord 70a is connected to the high-frequency power supply device 70. The high-frequency wiring cord 70a is electrically connected to the needle scalpel 102 provided within the insulation sheath 101 via the slider 55. With the high-frequency power supply device 70 according to the present embodiment, a foot switch 71 is provided, and a high-frequency current is supplied to the needle scalpel 102 by operating the foot switch 71. In a state in which the tip face of the needle scalpel 102 is disposed tightly against tissue, upon a high-frequency current being supplied to the needle scalpel 102, the tissue is subjected to marking.

Note that the tip of the needle scalpel 102 of the marking device 50F according to the present embodiment is provided with a sensor (not shown) for detecting the pressure value when the needle scalpel 102 is disposed tightly against tissue based on change in a resistance value. The detection value of this sensor is arranged to be output to the first sensor obtaining unit 23f.

With the endoscope system 1 wherein the handle portion 53f of the marking device 50F is disposed in the electrically-driven operation device 30, a marking program is activated by the surgeon pushing in and operating the programmed instruction unit 6 provided in the operation instructing device 2. In a programmed-control state, the operating lever 5a according to the present embodiment serves as a selection switch. Specifically, upon the operating lever 5a being leaned and operated, for example, to the reference mark F side, the insulation sheath 101 is advanced, a state in which the needle scalpel 102 being against tissue is kept for a predetermined period of time, and subsequently, a marking instructing signal serving as an instructing signal for retreating the insulation sheath 101 is output.

Figure 33A:
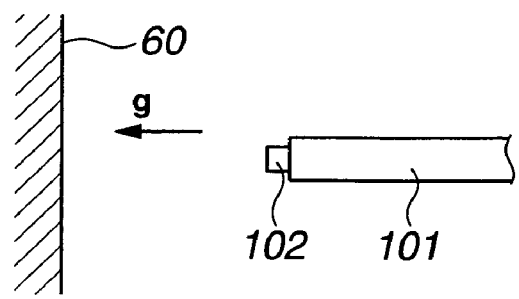
FIG. 33A is a diagram describing a state when determination is made regarding whether to perform marking manually or by programmed control.

The surgeon inserts the insertion unit 11 of the endoscope 10 toward a target portion within a body cavity of a subject while observing an endoscope image. Subsequently, the surgeon confronts the tip portion 11a of the insertion unit 11 with the tissue 60 as illustrated in FIG. 33A while confirming an endoscope image on the screen. Subsequently, the surgeon disposes the tip face of the needle scalpel 102 in the vicinity of the target portion of the tissue 60 by the surgeon's side operation while observing an endoscope image. Here, in the event of desiring an operation by programmed control, the surgeon pushes in and operates the programmed instruction unit 6 provided in the operation instructing device 2. Thus, the CPU 21 selects and executes the marking program registered on the storage device 22 as shown in steps S5 through S7 in FIG. 10 to enter a programmed-control state.

Figure 33B:
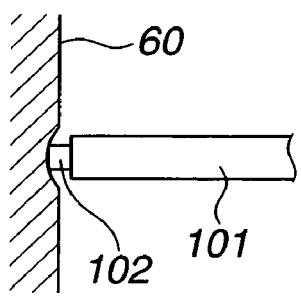
FIG. 33B is a diagram describing a state in which the needle scalpel is pressed against tissue in a programmed-control state.

In this programmed-control state, when performing marking, the surgeon leans and operates the operating lever 5a to the reference mark F side in a state in which the foot switch 71 is pushed in and operated. Then, a marking instructing signal is input to the manually-driven signal processing unit 23a. Then, the needle scalpel 102 moves to the tissue side, and the tip face of the needle scalpel 102 is in a state of pressing the tissue 60 such as illustrated in FIG. 33B. Then, the electric signal output from the sensor is input to the CPU 21.

Here, the CPU 21 outputs the input electric signal to the computing processing unit 21b, obtains pressing pressure, outputs the obtained pressing pressure to the determining unit 21c, and determines whether or not the pressing pressure is pressure suitable for marking. Then, the CPU 21 performs adjustment of the insulation sheath 101 based on the determination result, and makes the tip face of the needle scalpel 102 a state of being against the tissue 60 only for a predetermined period of time. During this period of time, the foot switch 71 is pushed in and operated by the surgeon, and thus, a high-frequency current is electrically conducted to the needle scalpel 102 disposed tightly with the tissue 60.

Thus, the surgeon operates the programmed operation instructing unit, and the CPU 21 is changed into a control state by the marking program, whereby even a physician who is inexperienced in treatment can perform marking in a sure manner by supplying a high-frequency current to tissue in the most appropriate state for the most appropriate period of time, as with a physician who is experienced in treatment.

Also, with the marking program according to the present embodiment, pressing pressure is detected, and a high-frequency current is supplied to the needle scalpel 102 only for a predetermined period of time, thereby subjecting tissue to desired marking.

Note that an arrangement may be made wherein when retreating the insulation sheath 101 by performing the above origin processing in a programmed-control state, the insulation sheath 101 is controlled so as to return to the origin.

Also, an arrangement may be made wherein the surgeon determines whether the state in which the needle scalpel 102 is pressed against tissue is good or bad without providing the sensor for detecting a pressure value. In this case, following determining that a state of the needle scalpel being pressed is good, the surgeon steps upon the foot switch, and simultaneously operates the programmed instruction unit 6 to activate the program. Then, following predetermined time elapsing, the sheath retreats, and tissue is subjected to marking.

FIG. 34 relates to a modification of the endoscope system including the marking device 50F. An endoscope system ID includes the above foot switch 71, but on the other hand, the high-frequency power supply device 70 and the control device 20 are electrically connected with a signal cable 70b. The control device 20 is provided with a high-frequency power-supply-device control-signal output unit serving as a third output unit 24c. Accordingly, a control signal is output to the high-frequency power supply device 70 from the third output unit 24c under control of the CPU 21, thereby supplying a high-frequency current to the needle scalpel 102.

With the endoscope system 1 wherein the handle portion 53 of the marking device 50G is disposed in the electrically-driven operation device 30, the marking program is activated by the surgeon pushing in and operating the programmed instruction unit 6 provided in the operation instructing device 2. In a programmed-control state, the operating lever 5a according to the present embodiment loses a function as the operating lever 5a, and also a function as a selection switch. In addition, the foot switch 71 also loses the function thereof.

Figure 35:
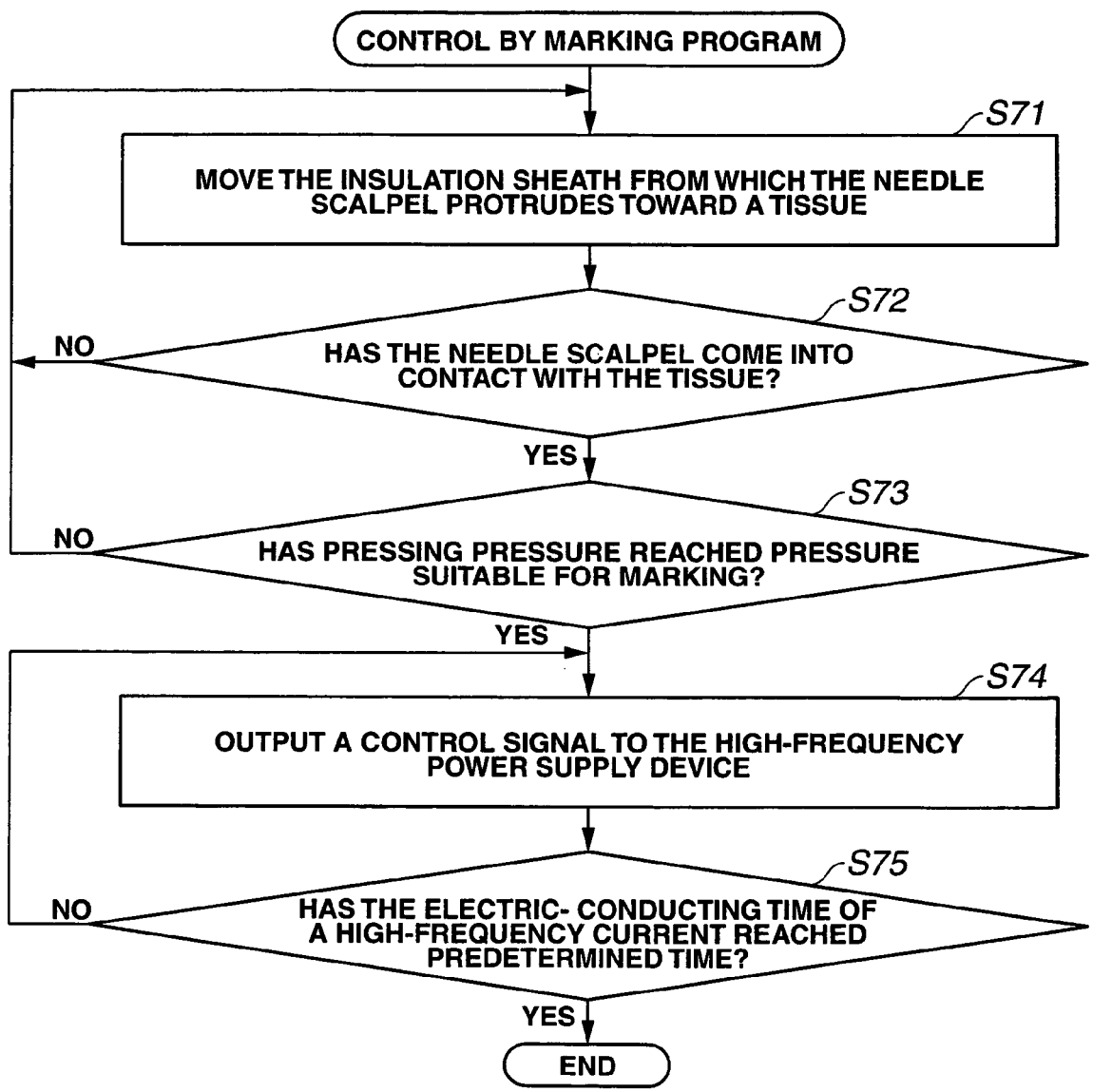
FIG. 35 is a diagram describing a control example using a marking program.

A programmed control example of the marking device 50G thus configured will be described with reference to FIG. 35.

The surgeon inserts the insertion unit 11 of the endoscope 10 toward the inside of a subject while observing an endoscope image. Subsequently, the surgeon disposes the tip face of the needle scalpel 102 so as to face the target portion of the tissue 60 such as illustrated in FIG. 33A by the surgeon's side operation while confirming an endoscope image on the screen.

Here, in the event of desiring an operation by programmed control, the surgeon pushes in and operates the programmed instruction unit 6 provided in the operation instructing device 2. Then, the marking program is activated. As shown in step S71 in FIG. 35, the CPU 21 performs control for moving the insulation sheath 101 from which the needle scalpel 102 protrudes toward the tissue 60, i.e., in the arrow g direction, such as illustrated in FIG. 33A. Subsequently, the CPU 21 monitors whether or not the electric signal to be output from the sensor provided in the needle scalpel 102 is input to the first sensor obtaining unit 23f as shown in step S72.

Upon confirming that the electric signal output from the sensor is input to the first sensor obtaining unit 23f in step S72, the CPU 21 proceeds to step S73. In step S73, the CPU 21 outputs the electric signal of the sensor to the computing processing unit 21b to obtain pressing pressure, and outputs the pressing pressure to the determining unit 21c to determine whether or not the pressing pressure has reached the pressure suitable for marking.

In step S73, the CPU 21 continuously outputs a control signal for moving the needle scalpel 102 in the arrow g direction until the pressing pressure has reached the pressure suitable for marking. Subsequently, as shown in step S73, upon determining that the pressing pressure has reached the pressure suitable for marking, as shown in step S74, the CPU 21 outputs a control signal to the high-frequency power supply device 70 from the third output unit 24c, and performs control for electrically conducting a high-frequency current as to the needle scalpel 102 for a predetermined period of time.

Figure 33C:
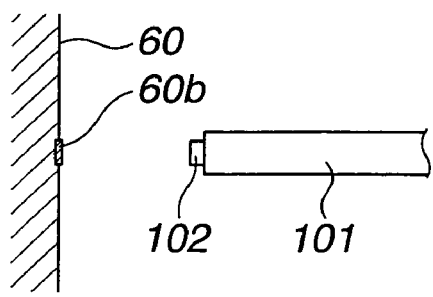
FIG. 33C is a diagram describing a marking portion formed in a programmed-control state.

Subsequently, the CPU 21 proceeds to step S75 to measure the electric conductive period of time of a high-frequency current. Subsequently, the CPU 21 electrically conducts a high-frequency current until the electric conductive period of time has reached a predetermined period of time, and upon reaching a predetermined period of time, the CPU 21 ends programmed control. Subsequently, the surgeon retreats the insulation sheath 101 in a manually-driven operating state. Thus, the marking portion 60b is formed on the tissue such as illustrated in FIG. 33C.

Thus, the surgeon operates the programmed operation instructing unit, and the needle scalpel is controlled and operated by the marking program, and also a high-frequency current is output. Thus, even a physician who is inexperienced in treatment can perform marking in a sure manner by supplying a high-frequency current to tissue in the most appropriate state for the most appropriate period of time, as with a physician who is experienced in treatment.

Also, with the marking program according to the present embodiment, pressing pressure is detected, and a high-frequency current is supplied only for a predetermined period of time, whereby subjecting tissue to desired marking.

Note that with the present embodiment, control for changing the electric conductive period of time of a high-frequency current is performed by pressing pressure, whereby tissue can be subjected to more appropriate marking. Also, an arrangement may be made wherein the above origin processing is performed, and retreat operation of the insulation sheath 101 is performed by programmed control.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system comprising:
   a treatment tool having a treatment-tool insertion unit to be inserted in a treatment-tool channel provided in an insertion unit of an endoscope and a function unit having a function for performing a certain treatment, which is introduced within a body cavity, provided at the tip side of the treatment-tool insertion unit;
   an electrically-driven operation device which electrically drives the function unit;
   an electrically-driven advance/retreat device which electrically drives the treatment-tool insertion unit;
   a control device, which is electrically connected to the electrically-driven advance/retreat device and the electrically-driven operation device, the control device including a control unit for outputting a control signal to the electrically-driven advance/retreat device and the electrically-driven operation device, and an operating program corresponding to a predetermined use of the treatment tool;
   an operation instructing device, which is electrically connected to the control device, the operating instructing device including a first operating instruction unit for outputting a first instruction signal for placing the electrically-driven operation device and the electrically-driven advance/retreat device into a manually-driven operating state, and a second operating instruction unit for outputting a second instruction signal for placing the electrically-driven operation device and the electrically-driven advance/retreat device into a programmed-control state by the operating program;
   wherein, when receiving a first instruction signal output from the operation instructing device, the control unit of the control device outputs the control signal corresponding to the first instruction signal to at least one of the electrically-driven advance/retreat device and the electrically-driven operation device, and when receiving a second instruction signal output from the operation instructing device, the control unit of the control device executes the operating program, and outputs the control signal in accordance with an instruction of the operating program to at least one of the electrically-driven advance/retreat device, and the electrically-driven operation device.

2. The endoscope system according to claim 1, wherein when receiving a first instruction signal output from the operation instructing device, and a second instruction signal output from the operation instructing device simultaneously, the control unit of the control device cancels the first instruction signal, and the second instruction signal.

3. The endoscope system according to claim 1, wherein the control unit of the control device includes a determining unit, and wherein the determining unit determines a running state of the electrically-driven operation device, and based on a determination result of the determining unit, the control unit outputs a control signal for operating the electrically-driven advance/retreat device, or the determining unit determines a running state of the electrically-driven advance/retreat device, and based on a determination result of the determining unit, the control unit outputs a control signal for operating the electrically-driven operation device.

4. The endoscope system according to claim 1, wherein the control unit of the control device includes a determining unit, and performs control for linking operation of the electrically-driven operation device with operation of the electrically-driven advance/retreat device.

5. The endoscope system according to claim 1, wherein the function unit of the treatment tool comprising at least one of:
   first detection means for detecting a running state by the electrically-driven advance/retreat device; and
   second detection means for detecting a running state by the electrically-driven operation device;
   wherein based on the detection result of the first detection means, or the detection result of the second detection means, the control unit outputs a control signal for instructing operation according to the detection result to at least one of the electrically-driven advance/retreat device and the electrically-driven operation device.

6. The endoscope system according to claim 5, wherein the function unit of the treatment tool is a tissue sampling unit;
   and wherein when receiving the detection result of the first detection means, the control unit outputs a control signal for changing the tissue sampling unit from an open state to a closed state, and when receiving the detection result of the second detection means, the control unit outputs a control signal for holding the tissue sampling unit, which has been changed at least from an open state to a closed state, in a closed state.

7. The endoscope system according to claim 5, wherein the function unit of the treatment tool is a tissue sampling unit;
   and wherein based on the detection result to be output from the first detection means, the control unit outputs a control signal for changing the tissue sampling unit from an open state to a closed state, and a control signal for holding tissue in a held state between the tissue sampling unit.

8. The endoscope system according to claim 7, wherein the control unit of the control device includes a computing processing unit for computing the amount of operation of the electrically-driven operation device and the electrically-driven advance/retreat device;
   and wherein based on the computation results of the computing processing unit, the control unit outputs the control signal corresponding to the computation result to at least one of the electrically-driven operation device and the electrically-driven advance/retreat device.

9. The endoscope system according to claim 1, wherein the control unit of the control device includes a determining unit;
   and wherein the control unit outputs a control signal to at least one of the electrically-driven operation device and the electrically-driven advance/retreat device based on results compared and determined by the determining unit between the amount of operation of the electrically-driven operation device and the amount set by the operating program, or results compared and determined by the determining unit between the amount of operation of the electrically-driven advance/retreat device and the amount set by the operating program.

10. The endoscope system according to claim 1, wherein when the treatment tool is a biopsy-forceps, the control unit comprises the following control steps:

a step for holding a tissue sampling unit serving as the function unit in an open state, and moving the tissue sampling unit toward tissue;

a step for changing the tissue sampling unit from an open state to a closed state; and a step for holding the tissue sampling unit in a closed state.

11. The endoscope system according to claim 10, further comprising:

a step for performing processing for setting a point, where the second instruction signal is output, as a point of origin; and a step for holding the tissue sampling unit in a closed state includes operation for moving the tissue sampling unit in a closed state to the point of origin.

12. The endoscope system according to claim 10, wherein in the step for changing the tissue sampling unit from an open state to a closed state, the tissue sampling unit is in a stopped state.

13. The endoscope system according to claim 10, wherein in the step for changing the tissue sampling unit from an open state to a closed state, the tissue sampling unit continues to move.

14. The endoscope system according to claim 1, wherein, when the treatment tool is a high-frequency snare, the control unit comprises the following control steps:

a step for matching movement in one direction of a snare portion serving as the function unit, and movement in the opposite direction as to the above one direction of the treatment-tool insertion unit; and a step for determining whether or not movement in one direction of a snare portion serving as the function unit, and movement in the opposite direction as to the above one direction of the treatment-tool insertion unit match.

15. The endoscope system according to claim 1, wherein, when the treatment tool is a basket-forceps, the control unit comprises the following control steps:

a step for placing a basket serving as the function unit into an open state, and retreating the basket at a constant speed to take in a calculus while rotating the basket at a constant speed; and a step for setting a rotating state of the basket to a constant state, and also setting a retreating state of the basket to a constant state.

16. The endoscope system according to claim 1, wherein, when the treatment tool is a basket-forceps, the control unit comprises the following control steps:

a step for taking in a calculus by changing the interval between the wires making up the basket to an expanded state or a narrowed state while rotating a basket serving as the function unit;

a step for storing the calculus taken in the inside of the basket within the basket, and retreating the basket storing the calculus at a constant speed while rotating the basket at a constant speed; and a step for setting a rotating state of the basket to a constant state, and also setting a retreating state of the basket to a constant state.

17. The endoscope system according to claim 1, wherein, when the treatment tool is an injector, the control unit comprises the following control steps:

a step for moving a needle tip of a needle tube making up an injector serving as the function unit toward tissue;

a step for monitoring a detection signal to be output from detection means provided at the needle tip to be punctured into the tissue;

a step for determining the amount of insertion of the needle tip based on the detection signal to be output from the detection means; and a step for moving an inner cylinder of the injector to inject the amount of liquid, which is set, into tissue.

18. The endoscope system according to claim 1, wherein, when the treatment tool is a spray tool, the control unit comprises the following control steps:

a step for retreating the treatment-tool insertion unit inserted into a body cavity at a constant speed, and also moving the piston of a syringe at a constant speed to spray pigment; and a step for monitoring whether or not the amount of retreat of the treatment-tool insertion unit has reached a predetermined distance.

19. The endoscope system according to claim 1, wherein, when the treatment tool is a marking tool, the control unit comprises the following control steps:

a step for moving the treatment-tool insertion unit from which a needle scalpel protrudes toward tissue;

a step for monitoring a detection signal to be output from detection means provided at the needle scalpel;

a step for determining the pressing pressure of the needle scalpel as to tissue based on the detection signal to be output from the detection means;

a step for outputting a control signal for electrically conducting a high-frequency current to the needle scalpel from a high-frequency power supply device for predetermined time; and a step for determining whether or not the electrically conducting time has reached the predetermined time.

20. The endoscope system according to claim 19, wherein, when the treatment tool is a marking tool, the control unit comprises the following control steps:

a step for outputting a control signal for electrically conducting a high-frequency current to the needle scalpel from a high-frequency power supply device for predetermined time; and a step for retreating the treatment-tool insertion unit a predetermined distance at a constant speed following the predetermined time elapsing.

* * * * *